United States Patent
Voytik-Harbin

(10) Patent No.: US 10,314,940 B2
(45) Date of Patent: Jun. 11, 2019

(54) COLLAGEN-BASED THERAPEUTIC DELIVERY SYSTEMS

(71) Applicant: Purdue Research Foundation Office of Technology Commercialization, West Lafayette, IN (US)

(72) Inventor: Sherry Voytik-Harbin, Zionsville, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/505,046

(22) PCT Filed: Aug. 27, 2015

(86) PCT No.: PCT/US2015/047176
§ 371 (c)(1),
(2) Date: Feb. 17, 2017

(87) PCT Pub. No.: WO2016/033322
PCT Pub. Date: Mar. 3, 2016

(65) Prior Publication Data
US 2017/0274120 A1  Sep. 28, 2017

Related U.S. Application Data

(60) Provisional application No. 62/042,664, filed on Aug. 27, 2014.

(51) Int. Cl.
| | | |
|---|---|---|
| *A61K 47/42* | (2017.01) | |
| *A61K 9/00* | (2006.01) | |
| *A61L 27/24* | (2006.01) | |
| *A61L 27/54* | (2006.01) | |
| *A61K 9/19* | (2006.01) | |
| *A61K 38/18* | (2006.01) | |

(52) U.S. Cl.
CPC ............ *A61L 27/24* (2013.01); *A61K 9/0024* (2013.01); *A61K 9/19* (2013.01); *A61K 38/18* (2013.01); *A61K 47/42* (2013.01); *A61L 27/54* (2013.01); *A61L 2300/414* (2013.01); *A61L 2300/604* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 9,867,905 B2 * | 1/2018 | Voytik-Harbin | ........ A61L 27/24 |
| 2009/0269386 A1 | 10/2009 | Zubery et al. | |
| 2009/0280180 A1 * | 11/2009 | Voytik-Harbin | ........ A61L 27/24 |
| | | | 424/484 |
| 2010/0119578 A1 | 5/2010 | To et al. | |
| 2011/0020418 A1 * | 1/2011 | Bosley, Jr. | .............. A61L 27/26 |
| | | | 424/422 |
| 2014/0094617 A1 | 4/2014 | Dubois | |
| 2014/0193473 A1 | 7/2014 | Yoder et al. | |
| 2016/0186131 A1 * | 6/2016 | Voytik-Harbin | ........ A61L 27/24 |
| | | | 424/93.7 |

FOREIGN PATENT DOCUMENTS

| | | |
|---|---|---|
| WO | WO 2012/004564 A1 | 1/2012 |
| WO | WO-2014121067 A1 * | 8/2014 ............. C07K 14/78 |

OTHER PUBLICATIONS

International Search Report and Written Opinion issued by the ISA/US, Commissioner for Patents, dated Jan. 19, 2016, for International Application No. PCT/US2015/047176; 12 pages.
Whittington, Catherine, F., et al., "Oligomers Modulate Interfibril Branching and Mass Transport Properties of Collagen Matrices", Microsc Microanal, vol. 19, No. 5, Oct. 2013, 20 pages.
International Preliminary Report on Patentability issued by The International Bureau of WIPO, dated Feb. 28, 2017, for International Application No. PCT/US2015/047176; 11 pages.

* cited by examiner

*Primary Examiner* — Abigail Vanhorn
(74) *Attorney, Agent, or Firm* — Faegre Baker Daniels LLP

(57) ABSTRACT

A collagen-based therapeutic delivery device includes an insoluble synthetic collagen-fibril matrix comprising a polymerization product of soluble oligomeric collagen or a polymerization product of a mixture of soluble oligomeric collagen with one or more type of non-oligomeric soluble collagen molecules, such as, for example, soluble telocollagen and/or soluble atelocollagen, and an active agent dispersed throughout the collagen-fibril matrix or within a portion of the collagen-fibril matrix. A pre-matrix composition includes an aqueous solution including soluble collagen-fibril building blocks and an active agent in the aqueous solution. The soluble collagen-fibril building blocks include soluble oligomeric collagen or a mixture of soluble oligomeric collagen with non-oligomeric soluble collagen molecules. The building blocks are operable to self-assemble into a macromolecular synthetic collagen-fibril matrix in the absence of an exogenous cross-linking agent. Methods of making and using the pre-matrix composition and the device are also provided.

13 Claims, 19 Drawing Sheets

Fig. 2. Size of fluorescein, 10 kDa, 150 kDa, 500 kDa, and 2000 kDa FITC-Dex (FD) relative to clinically important drug categories.

COLLAGEN-BASED THERAPEUTIC DELIVERY SYSTEMS

CROSS-REFERENCE TO RELATED APPLICATIONS

This application is a national stage filing of PCT International Application Serial No. PCT/US2015/047176, filed Aug. 27, 2015, which claims the benefit of U.S. Provisional Patent Application Ser. No. 62/042,6640, filed Aug. 27, 2014, entitled "Drug Delivery System," the disclosures of which are expressly incorporated by reference herein in their entireties.

GOVERNMENT SUPPORT

This invention was made with government support under NIH HL109602 awarded by the National Institutes of Health. The government has certain rights in the invention.

TECHNICAL FIELD

The present disclosure generally relates to a therapeutic delivery device comprising a synthetic collagen-fibril matrix with an active agent dispersed therein, a pre-matrix solution operable for making a delivery device and methods for active agent delivery. The disclosure also relates to methods of customizing a delivery system by controlling one or more of the proteolytic biodegradability properties of the collagen-fibril matrix, the microstructural properties of the collagen-fibril matrix, the mechanical properties of the collagen-fibril matrix and the transport properties of the collagen-fibril matrix.

BACKGROUND OF THE DISCLOSURE

Collagen, the major extracellular matrix (ECM) component of connective tissues, has received a great deal of attention as a candidate material for use as an implantable or injectable drug delivery vehicle, primarily because of its biocompatibility, low immunogenicity and biodegradability. Extracellular matrices are known to provide scaffolding for cells, while organizing the cells three-dimensionally and providing essential information to regulate cell behavior. As such, the field of tissue engineering strives to mimic both the form and function of these scaffolds to create compositions for optimal tissue repair and replacement. Collagen, and in particular type I collagen, may be used in the field of tissue engineering due to its high availability in the body, conservation across tissues and species, biodegradability and biocompatibility. In fact, not only is collagen the most abundant molecule of the ECM, it is responsible for the majority of the structural and mechanical properties of several tissues. The in vivo form of collagen is a triple-helix center region that is capped at both ends by randomly organized telopeptides. These collagen molecules are found within the ECM assembled as branched collagen-fibril networks that contain natural molecular cross-links.

In spite of numerous advantages and wide research on collagen as a natural biomaterial, its use as a vehicle for controlling local active agent release has been limited. Furthermore, its application as a tissue graft that induces appropriate tissue regeneration while at the same time achieving predictable localized delivery of specified agents has not been achieved to date. In fact, only a few collagen-based active agent delivery formulations have made it into clinical trials. Existing formulations can be categorized as either non-dissociated fibrillar collagens or solubilized collagens. These formulations have a number of shortcomings, including poorly defined molecular composition, low mechanical integrity, rapid biodegradation and limited control over drug release profiles.

Non-dissociated fibrillar collagens are formulations that contain decellularized collagen extracellular matrix (ECM) particulate matter, which is mechanically homogenized, acid-swollen, and finally lyophilized to form sponge that may or may not be cross-linked. Soluble collagens, by contrast, are obtained from pepsin or acid solubilization of mammalian tissues to form viscous collagen solutions, which are then lyophilized and formulated as a cross-linked or non-cross-linked sponge or injectable viscous gel. As stated above, previously-described collagen-based active agent delivery platforms have many limitations, including poorly defined molecular compositions, low mechanical integrity and stability, rapid proteolytic degradation rapid proteolytic degradation and limited design control. While exogenous crosslinking, including chemical and physical means, is routinely used to improve mechanical and handling properties as well as increase persistence upon implantation, such processing is associated with deleterious tissue responses and loss of biological activity.

The marginal success of these present day collagen-based drug delivery formulations can be traced to these major limitations. Moreover, these conventional formulations exhibit amorphous microstructures, with unsatisfactory control of material properties, including pore size and proteolytic degradability. Cursory control of these parameters is often achieved through modulation of lyophilization conditions and/or exogenous chemical and physical crosslinking. Materials formed without cross-linking represent viscous gels. They are characterized as mechanically unstable, too soft to handle, and unable to resist cell-induced contractions, thus failing to support cell ingrowth and migration required for tissue regeneration. On the other hand, exogenous cross-linking has been shown to have detrimental effects on cells and tissues, such as cytotoxicity or tissue calcification and partial denaturation of collagen itself. Aldehyde based cross-linking may lead to aldehyde residues in the final product and may influence the biocompatibility of the collagen. Moreover, de-hydrothermal cross-linking has natural limitations and does not lead to materials with sufficiently improved properties.

Accordingly, there is a need for further advancements in the design and development of local therapeutic delivery systems and integrated tissue regeneration. As will be explained in detail herein, the present disclosure addresses this need and also provides associated compositions, devices and methods that address deficiencies in the existing art.

SUMMARY OF THE DISCLOSURE

In accordance with one aspect of the present disclosure, a therapeutic delivery device is provided that includes an insoluble synthetic collagen-fibril matrix and an active agent dispersed throughout the collagen-fibril matrix or within a portion of the collagen-fibril matrix. The collagen-fibril matrix comprises a polymerization product of soluble oligomeric collagen or a polymerization product of a mixture of soluble oligomeric collagen with one or more other type of soluble collagen molecules, also referred to herein as non-oligomeric soluble collagen molecules. In one embodiment, the non-oligomeric soluble collagen molecules include one or more of soluble telocollagen molecules and soluble atelocollagen molecules. In one embodiment, the synthetic collagen-fibril matrix exhibits a stiffness of at least 5 Pa. The oligomeric collagen or mixture of soluble oligomeric collagen with one or more type of non-oligomeric soluble collagen molecules is capable of self-assembling into a synthetic macromolecular collagen-fibril matrix in the absence of an exogenous crosslinking agent.

In another aspect of the disclosure, a method for making a therapeutic delivery device is provided that includes (i) forming an aqueous solution comprising a quantity of soluble collagen-fibril building blocks; (ii) causing the building blocks to polymerize by self-assembly, thereby forming an insoluble synthetic collagen-fibril matrix; and (iii) either (a) including a quantity of an active agent in the aqueous solution whereby said causing forms a collagen-fibril matrix having the active agent dispersed therein or (b) contacting the synthetic collagen-fibril matrix with the quantity of the active agent to form a collagen-fibril matrix having the active agent dispersed therein. The quantity of building blocks comprises soluble oligomeric collagen. In one embodiment, the collagen-fibril matrix exhibits a stiffness of at least 5 Pa.

This disclosure also provides a pre-matrix composition that comprises an aqueous solution that includes soluble collagen-fibril building blocks and an active agent. The soluble collagen-fibril building blocks include soluble oligomeric collagen or a mixture of soluble oligomeric collagen with one or more type of non-oligomeric soluble collagen molecules, which are operable to self-assemble into a synthetic macromolecular collagen-fibril matrix in the absence of an exogenous cross-linking agent. In one embodiment, the non-oligomeric soluble collagen molecules include one or more of soluble telocollagen molecules and soluble atelocollagen molecules. In one embodiment, the agent is associated with one or more collagen-fibril building blocks. In one embodiment, the collagen-fibril matrix exhibits a stiffness of at least 5 Pa.

In another aspect of the disclosure, there is provided a method for delivering an active agent that includes positioning at an in situ location (i) a pre-matrix composition that comprises an aqueous solution that includes soluble collagen-fibril building blocks and an active agent; or (ii) a therapeutic delivery device that includes an insoluble synthetic collagen-fibril matrix and a first active agent dispersed throughout the collagen-fibril matrix or within a portion of the collagen-fibril matrix.

Still other embodiments and features of the application will become apparent from the following written description along with the accompanying figures.

BRIEF DESCRIPTION OF THE FIGURES

The various aspects of the present application will become more apparent and the teachings of the present application itself will be better understood by reference to the following description of the embodiments of the present application taken in conjunction with the accompanying drawings, wherein.

Figure 1:
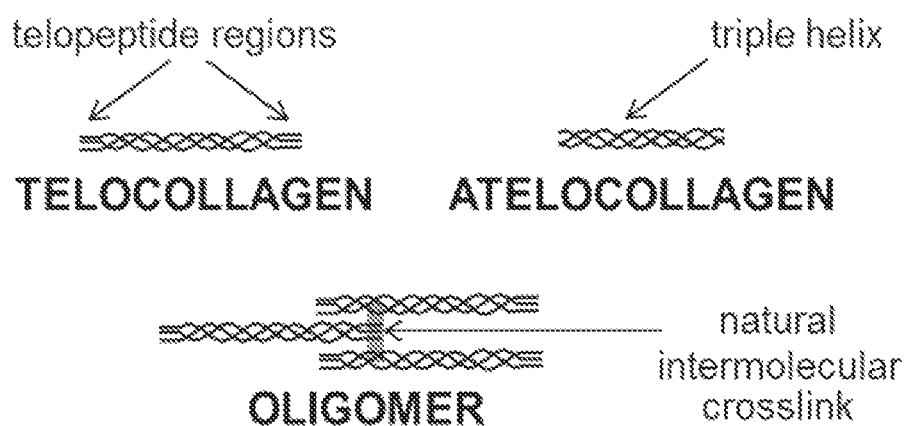
FIG. 1 depicts a schematic of example soluble building blocks of a collagen-fibril matrix in accordance with the teachings of the present disclosure.

Although the exemplification set out herein illustrates embodiments of the present application in several forms, the embodiments disclosed below are not intended to be exhaustive or to be construed as limiting the scope of the present application to the precise forms disclosed.

DETAILED DESCRIPTION

The embodiments of the present disclosure that are described herein are not intended to be exhaustive or to limit the teachings of the present application to the precise forms disclosed in the following detailed description. Rather, the embodiments are chosen and described so that others skilled in the art may appreciate and understand the principles and practices of the present disclosure.

Unless defined otherwise, all technical and scientific terms used herein have the same meaning as commonly understood by one of ordinary skill in the art to which this application pertains. Although methods and materials similar or equivalent to those described herein can be used in the practice or testing of the present application, various specific methods and materials are now described.

One aspect of the present disclosure is directed to a collagen-based therapeutic delivery device comprising an insoluble synthetic collagen-fibril matrix with an active agent dispersed therein. In another aspect, the disclosure is directed to a pre-matrix composition. In still other aspects, the disclosure provides methods of making and using the therapeutic delivery device and the pre-matrix composition. In accordance with certain embodiments of the present disclosure, an illustrative therapeutic delivery device is prepared by polymerizing defined mixtures of collagen-fibril matrix building blocks from aqueous solution. The collagen based therapeutic delivery device can be implantable or injectable. The disclosed systems enable a broad range of customizable spatiotemporal molecular release profiles for one or more therapeutics, referred to herein as active agents, including burst, sustained and targeted release.

As used herein, the term "collagen-fibril matrix" or "collagen-fibril material" refers to a Type I collagen composition that includes collagen fibrils and that has been formed under controlled conditions from solubilized collagen building blocks. In one embodiment, at least 1% of the collagen in the collagen-fibril matrix is composed of oligomers. In other embodiments, at least 2%, at least 3%, at least 4% or at least 5% of the collagen in the collagen-fibril matrix is composed of oligomers. In one embodiment, the collagen-fibril matrix material has a stiffness of at least 5 Pa. In other embodiments the collagen-fibril matrix material has a stiffness of at least 10 Pa, at least 15 Pa, at least 20 Pa or at least 25 Pa.

As used herein, the term "collagen" refers to a family of at least 20 genetically different secreted proteins that serve a predominantly structural function and possess a unique triple helical structure configuration of three polypeptide units known as alpha chains. The three alpha chains (two α1 (I) and one α2(I) chain) are characterized by (Gly-X-Y)$_n$ repeat units where the X and Y positions are often occupied by proline and hydroxyproline forming an approximately 300 nm long triple helical collagen molecule flanked on each end by a non-helical telopeptide end. These collagen molecules, also known as monomers, are the fundamental building blocks that self-assemble in a hierarchical fashion to form tissue-specific networks of micro-fibrils, fibrils, fiber and fiber bundles that then combine to form the ECM of the body's tissues. Lysyl oxidase binds to and catalyzes cross-link formation between prefibrillar aggregates of staggered collagen molecules (called monomers) to create covalently cross-linked dimers or trimers (called oligomers). The different oligomer precursors modulate the progressive molecular packing and assembly that eventually yields tissue-specific fibril architecture and matrix function. Both monomer and oligomer formulations possess intact telopeptide regions and contain reactive aldehydes generated from acid-labile, intermediate cross-links. Proteolytic enzyme treatment of collagen removes the terminal telopeptide regions to yield atelocollagen formulations, whereas removal of the amino and carboxyl-telopeptides results in an amorphous arrangement of collagen molecules and loss of the banded-fibril pattern in a reconstituted product.

As used herein, the term "oligomer" refers to a molecule in which two or more tropocollagen molecules are covalently attached to one another via a naturally occurring intramolecular cross-link and which is soluble in an aqueous fluid.

As used herein, the term "telocollagen" (also referred to as "tropocollagen", "telomer", a "collagen monomer" or "monomeric collagen") refers to an individual collagen molecule in which carboxy- and amino-terminal non-helical telopeptide ends are intact; which is able to undergo self-assembly into a fibrillar matrix, and which lacks intermolecular covalent cross-links.

As used herein, the term "telopeptide" refers to amino- and carboxy-terminal non-triple helical domains of tropocollagen strands known to be important to fibrillogenesis, polymerization and lysyl-oxidase mediated intermolecular cross-link formation.

As used herein, the term "atelocollagen" refers to a triple helix molecule in which the telopeptide regions have been partially or completely removed from tropocollagen. Such atelocollagen preparations are typically the outcome of enzyme-based (for example, pepsin-based) collagen extraction procedures from tissues.

As used herein, the term "collagen mimetic peptides" refers to chemically-synthesized collagen building blocks having specific amino acid sequences representing the triple helical portion of collagen, often -(Pro-Hyp-Gly)-, forms a triple helix conformation that resembles that found in natural collagens.

As used herein, the term "matrix" refers to a loose meshwork within which cells are or can be embedded or an arrangement of connected things. In the context of collagen, matrix refers to a composite material composed of an insoluble collagen-fibril network or amorphous nanostructure surrounded by an interstitial fluid phase.

It should be understood and appreciated herein that oligomers comprise small aggregates of collagen molecules (e.g., dimers or trimers), which retain collagen's tissue-specific, covalent intermolecular cross-links, whereas telocollagen (or monomers) are individual collagen molecules that lack these intermolecular covalent cross-links. Telocollagen and oligomers possess intact telopeptide regions and contain reactive aldehydes generated from acid-labile, intermediate cross-links. Upon natural in vivo polymerization, the process through which collagen fibrils assemble to form a fibril polymeric network, these reactive aldehydes spontaneously reform covalent, intermediate cross-links as part of the fibril-forming process. Pepsin-solubilized (telopeptide-deficient) atelomer (or atelocollagen) formulations are created when collagen is treated with proteolytic enzymes that remove the terminal telopeptide regions. As both the amino (N)- and carboxyl (C)-telopeptides play important roles in cross-linking and fibril formation, their complete removal results in an amorphous arrangement of collagen molecules and a consequent loss of the banded-fibril pattern in a reconstituted product.

The collagen matrix building blocks, including oligomers, telocollagen and atelocollagen, may be obtained from a wide variety of raw collagen sources known in the art including, but not limited to, mammalian tissues, such as bovine, porcine and equine hides and tendons, and human tendons. Alternatively, the building blocks can be collagen mimetic peptides or soluble collagen molecules produced using recombinant technology. The matrices formed from these building blocks as described in the present disclosure exhibit superior mechano-biological properties as compared to commercially available collagen formulations. The matrices described herein also exhibit different properties than raw or native collagen. Type I collagen polymers in oligomer form are a primary building block of the insoluble synthetic collagen-fibril matrix described herein. As further described herein, the ratio of oligomer to non-oligomeric soluble collagen molecules, such as, for example, atelocollagen and/or telocollagen, can be varied to modulate various properties of the formed collagen-fibril matrix, which enables customization of a collagen-based therapeutic delivery device as disclosed herein depending on the intended purpose, location and placement of the device.

As indicated above, in addition to the collagen-fibril matrix, the collagen-based therapeutic delivery device also includes an active agent or, optionally, more than one active agent. The one or more active agent included in the device also can vary depending on the intended purpose, location and placement of the device. As used herein, the term "active agent" refers to any compound, agent, molecule, biomolecule, drug, therapeutic agent, nanoparticle, peptide, protein, polypeptide, antibody, ligand, partial antibody, steroid, growth factor, transcription factor, DNA, RNA, virus, bacteria, lipid, vitamin, small molecule, or large molecule that has activity in a biological system. Active agents include but are not limited to "biomolecules", "drugs", silver amine complexes, surfactants, polyhexamethylene biguanidine, betaine, antimicrobials, linear polymer biguanidines with a germicidal activity, bioactive additives, heparin, glyosaminoglycans, extracellular matrix proteins, antibiotics, growth factors, epidermal growth factor (EGF), platelet derived growth factor (PDGF), fibroblast growth factor (FGF), collagen binding peptides or factors, connective tissue activating peptides (CTAP), transforming growth factors (TGFs), oncostatic agents, immunomodulators, immunomodulating agents, anti-inflammatory agents, osteogeneic agents, hematopoietic agents, hematopoietic modulators, osteoinductive agents, TGF-β1, TGF-β2, TGFα, insulin-like growth factors (IGFs), tumor necrosis factors (TNFs), interleukins, IL-1, IL-2, colony stimulating factors (CSF), G-CSF, GM-CSF, erythropoietin, nerve growth factors (NGF), interferons (IFN), IFN-α, IFN-β, IFN-γ, preservatives, dyes, non-bioactive agents, hormones and synthetic analogs of the above. "Biomolecules" include, but are not limited to, steroids, growth factors, transcription factors, DNA, RNA (including siRNA, mRNA etc), peptides (natural and synthetic), proteins, partial or whole antibodies, ligands, viruses, bacteria, lipids, or vitamins. "Drugs" include but are not limited to "small molecules" including but not limited to chemotherapeutics, inhibitors, stimulators, proteases, antibiotics, antivirals; "biomolecules", "large molecules" or a combination thereof and wherein the drug is used to have a beneficial or negative effect on the target protein, cell or tissue. Surfactants may include, but are not limited to, glycine derivatives, sulfosuccinate, and an amide based on an unbranched fatty acid.

As used herein, the term "immunomodulatory amount" refers to an amount of a particular agent or factor sufficient to show a demonstrable effect on the subject's immune system. Immunomodulation may suppress or enhance the immune system as desired by a practitioner. Suppressing the immune system may be desirable when the subject is an organ transplant recipient or for treatment of autoimmune disease including but not limited to lupus, autoimmune arthritis, autoimmune diabetes; additional diagnoses in which suppression of the immune system is desirable are known to those skilled in the art. Alternatively, immunomodulation may enhance the immune system for example in the treatment of cancer, serious infection or wound repair; additional diagnoses in which enhancement of the immune system is desirable are known to those skilled in the art.

As used herein, the term "oncostatically effective amount" is an amount of an agent which is capable of inhibiting tumor cell growth in a subject having tumor cells sensitive to the selected agent.

As used herein, the term "hematopoietically modulatory amount" is that amount of an agent which enhances or inhibits the production and/or maturation of bloods cells.

As used herein, the term "osteoinductive amount" is that amount of an agent which causes or contributes to a measurable increase in bone growth or rate of bone growth.

The collagen-fibril matrix building blocks used to construct the collagen compositions described herein can be obtained from a number of sources, including, for example, porcine skin. Suitable tissues useful as a collagen-containing source material for isolating collagen or collagen components to make the collagen compositions described herein include submucosa tissues or any other extracellular matrix-containing tissues of a warm-blooded vertebrate. Suitable methods of preparing submucosa tissues are described in U.S. Pat. Nos. 4,902,508; 5,281,422 and 5,275,826, the disclosures of which are each incorporated herein by reference in their entirety. Extracellular matrix material-containing tissues other than submucosa tissue may be used to obtain collagen in accordance with still other embodiments disclosed herein. Method of preparing other extracellular matrix material-derived tissues for use in obtaining purified collagen or partially purified extracellular matrix components are known to those skilled in the art. For example, see U.S. Pat. No. 5,163,955 (pericardial tissue); U.S. Pat. No. 5,554,389 (urinary bladder submucosa tissue); U.S. Pat. No. 6,099,567 (stomach submucosa tissue); U.S. Pat. No. 6,576,265 (extracellular matrix tissues generally); U.S. Pat. No. 6,793,939 (liver basement membrane tissues); and U.S. Pat. No. 7,919,121 (liver basement membrane tissues); and International PCT Publication No. WO 2001/45765 (extracellular matrix tissues generally), each incorporated herein by reference. In various other embodiments, the collagen-containing source material can be selected from the group consisting of placental tissue, ovarian tissue, uterine tissue, animal tail tissue, skin tissue, bone, tendon and cartilage tissue. In some embodiments, the collagen is selected from pig skin collagen, bovine collagen and human collagen; however, it should be understood and appreciated herein that any suitable extracellular matrix-containing tissue can be used as a collagen-containing source material to isolate purified collagen or partially purified extracellular matrix components in accordance with the present teachings.

An illustrative preparation method for preparing submucosa tissues as a source of purified collagen or partially purified extracellular matrix components is described in U.S. Pat. No. 4,902,508, the disclosure of which is incorporated herein by reference. In one embodiment, a segment of vertebrate intestine, for example, preferably harvested from porcine, ovine or bovine species, but not excluding other species, is subjected to abrasion using a longitudinal wiping motion to remove cells or cell-removal is accomplished by hypotonic or hypertonic lysis. In one embodiment, the submucosa tissue is rinsed under hypotonic conditions, such as with water or with saline under hypotonic conditions and is optionally sterilized. In another illustrative embodiment, such compositions can be prepared by mechanically removing the luminal portion of the tunica mucosa and the external muscle layers and/or lysing resident cells with hypotonic or hypertonic washes, such as with water or saline. In these embodiments, the submucosa tissue can be stored in a hydrated or dehydrated state prior to isolation of the purified collagen or partially purified extracellular matrix components. In various aspects, the submucosa tissue can comprise any delamination embodiment, including the tunica submucosa delaminated from both the tunica muscularis and at least the luminal portion of the tunica mucosa of a warm-blooded vertebrate.

As indicated above, one building block used to prepare the collagen-fibril matrix is oligomeric collagen. The presence of oligomeric collagen enables the self-assembly of the building blocks into a collagen-fibril matrix and increases the assembly rate, yielding collagen compositions with distinct fibril microstructures and excellent mechanical integrity (e.g., stiffness).

In some embodiments, the building blocks for the collagen-fibril matrix also include various proportions non-oligomeric soluble collagen molecules. In one embodiment, the building blocks include one or both of telocollagen and/or atelocollagen. In certain embodiments, the building blocks include oligomeric collagen and atelocollagen. In other embodiments the building blocks include oligomeric collagen and telocollagen. In still other embodiments, the building blocks include oligomeric collagen, telocollagen, and atelocollagen. The amounts of oligomeric collagen, telocollagen, atelocollagen and/or other non-oligomeric soluble collagen molecules may be formulated in solution prior to initiation of polymerization to modulate one or more property of the resulting synthetic collagen-fibril matrix including, for example, stiffness, strength, fluid and mass transport, proteolytic degradation and/or compatibility. It is recognized that a predetermined ratio of oligomer to non-oligomeric soluble collagen molecules for use with a particular active agent may differ from that suitable for use with a different active agent.

Collagen concentration may be expressed in mass/volume or mass/mass. Collagen content may be measured by any means known in the art, including but not limited to, calibrated colorimetric assays such as Sirius red and amino acid analysis for hydroxyproline. Viscosity of collagen polymer formulations is impacted by a number of factors which may include, but are not limited to: solution or dispersion/suspension, concentration, molecular composition, molecular size, temperature and operating condition. Viscosity measurements may be obtained by any means known in the art including, but not limited to, a viscometer or rheometer.

The concentration of soluble collagen present in an aqueous pre-matrix composition used to make a synthetic collagen-fibril matrix can vary. In some embodiments, the collagen is present at a concentration of about 0.5 mg/ml to about 500 mg/ml. In other embodiments, the collagen is present at a concentration of about 0.5 mg/ml to about 400 mg/ml. In yet other embodiments, the collagen is present at a concentration of about 0.5 mg/ml to about 300 mg/ml. In some embodiments, the collagen is present at a concentration of about 0.5 mg/ml to about 200 mg/ml. In other embodiments, the collagen is present at a concentration of about 0.5 mg/ml to about 100 mg/ml. In yet other embodiments, the collagen is present at a concentration of about 1 mg/ml to about 5 mg/ml. In still yet other embodiments, the collagen is present at a concentration of about 2 mg/ml to about 5 mg/ml. In some embodiments, the collagen is present at a concentration of about 3.5 mg/ml. In other embodiments, the collagen is present at a concentration of about 4 mg/ml to about 10 mg/ml. In yet other embodiments, the collagen is present at a concentration of about 5 mg/ml. In some embodiments, the collagen is present at a concentration of about 10 mg/ml to about 20 mg/ml. In other embodiments, the collagen is present at a concentration of about 12 mg/ml. In yet other embodiments, the collagen is present at a concentration of about 20 mg/ml to about 30 mg/ml. In some embodiments, the collagen is present at a concentration of about 24 mg/ml. In some embodiments, the collagen is present at a concentration of about 500 mg/ml. In other embodiments, the collagen is present at a concentration of about 400 mg/ml. In yet other embodiments, the collagen is present at a concentration of about 300 mg/ml. In other embodiments, the collagen is present at a concentration of about 200 mg/ml. In yet other embodiments, the collagen is present at a concentration of about 100 mg/ml. In other embodiments, the collagen is present at a concentration of about 75 mg/ml. In yet other embodiments, the collagen is present at a concentration of about 50 mg/ml.

In the embodiments described herein, the synthetic collagen-fibril matrices can have an oligomer content quantified by average polymer molecular weight (AMW). As described herein, modulation of AMW can affect polymerization kinetics, fibril microstructure, molecular properties, and fibril architecture of the matrices, for example, interfibril branching, pore size, and mechanical integrity (e.g., matrix stiffness). In another embodiment, the oligomer content of the pre-matrix composition, as quantified by average polymer molecular weight, positively correlates with matrix stiffness.

In some embodiments, a non-oligomeric soluble collagen included in the pre-matrix composition is reduced collagen. As used herein "reduced collagen" means collagen that is reduced in vitro to eliminate or substantially reduce reactive aldehydes. For example, collagen may be reduced in vitro by treatment of collagen with a reducing agent (e.g., sodium borohydride).

In accordance with certain aspects of the present disclosure, a collagen-based therapeutic delivery device comprises a synthetic collagen-fibril matrix adapted for delivery of an active agent. The incorporation of an active agent may be achieved by several methods including, but not necessarily limited to, admixing the agent with soluble collagen-fibril matrix building blocks in a pre-matrix composition prior to polymerization, exposing an already-formed synthetic collagen-fibril material with an active agent following polymerization, and covalently attaching an active agent to a soluble collagen-fibril matrix building block and polymerizing the modified collagen building block, either alone or in the presence of unmodified collagen-fibril matrix building blocks. It should be understood and appreciated herein that the method of incorporating an active agent in the synthetic collagen-fibril matrix may vary based on the active agent. It is further recognized that the method of incorporating a first active agent in the collagen-fibril matrix may be the same or different from the method of incorporating a second active agent in the collagen-fibril matrix. It should also be understood and appreciated herein that the terms "first," "second," and "third" as applied to an active agent, are intended to allow distinctions between different active agents and do not necessarily convey a required chronological characteristic or order.

The purity of a collagen-fibril matrix in accordance with the teachings of the present disclosure may be evaluated by any means known in the art including, but not limited to, SDS-PAGE either on the collagen polymer directly or after specific enzymatic (bacterial collagenase) or chemical (cyanogen bromide) cleavage, peptide mapping, amino-terminal sequencing, and non-collagenous impurity assays. Methods of characterizing characteristics of a collagen-fibril matrix include, but are not limited to, cation-exchange HPLC, natural fluorescence, LC/MS, MS, dynamic light scattering, size-exclusion chromatography, viscosity measurements, circular dichroism, differential scanning calorimetry, trypsin susceptibility, impurity profiling, TEM, SEM, cryo-SEM, confocal microscopy, multiphoton microscopy and atomic force microscopy.

In accordance with certain aspects herein, qualitative and quantitative microstructural characteristics of a collagen-fibril matrix can be determined by environmental or cryostage scanning electron microscopy, transmission electron microscopy, confocal microscopy, second harmonic generation multi-photon microscopy. Tensile, compressive and viscoelastic properties can be determined by rheometry or tensile testing. All of these methods are known in the art or are further described in U.S. patent application Ser. No. 11/435,635 (published Nov. 22, 2007, as Publication No. 2007/0269476 A1), U.S. patent application Ser. No. 11/914,606 (published Jan. 8, 2009, as Publication No. 2009/0011021 A1), U.S. patent application Ser. No. 12/300,951 (published Jul. 9, 2009, as Publication No. 2009/0175922 A1), U.S. patent application Ser. No. 13/192,276 (published Feb. 2, 2012, as Publication No. 2012/0027732 A1), U.S. patent application Ser. No. 13/383,796 (published May 10, 2012, as Publication No. 2012/0115222 A1), or are described in Roeder et al., *J. Biomech. Eng.*, vol. 124, pp. 214-222 (2002), in Pizzo et al., *J. Appl. Physiol.*, vol. 98, pp. 1-13 (2004), Fulzele et al., *Eur. J. Pharm. Sci.*, vol. 20, pp. 53-61 (2003), Griffey et al., *J. Biomed. Mater. Res.*, vol. 58, pp. 10-15 (2001), Hunt et al., *Am. J. Surg.*, vol. 114, pp. 302-307 (1967), and Schilling et al., *Surgery*, vol. 46, pp. 702-710 (1959), the disclosures of which are each incorporated herein by reference in their entireties. Collagen characteristics and methods of characterizing collagen characteristics are discussed in ASTM International F3089-14, 2014 West Conshohocken Pa., the disclosure of which is herein incorporated by reference in its entirety.

In certain aspects of the present disclosure, the synthetic collagen-fibril matrix exhibits a stiffness of at least 5 Pa. In another embodiment, the synthetic collagen-fibril matrix exhibits a stiffness of between 5 Pa and 100 GPa. Stiffness may also be referred to as the elastic or linear modulus.

In some embodiments, the collagen-fibril matrix comprises a co-polymer, such collagen-fibril matrix being referred to herein as a "hybrid collagen-fibril" matrix. In one embodiment, the co-polymer comprises a polymerization product of a mixture of one or more types of soluble collagen building blocks with one or more synthetic or natural non-collagen molecule consisting of individual chemical moieties, which may be the different or the same. As used herein, the term "co-polymer" refers to individual chemical moieties that are joined end-to-end to form a linear molecule, as well as individual chemical moieties joined together in the form of a branched (e.g., a "multi-arm" or "star-shaped") structure. In alternative embodiments, the co-polymer comprises a copolymers that is obtained by copolymerization of two monomer species, obtained from three monomers species ("terpolymers"), obtained from four monomers species ("quaterpolymers") or obtained from more than four monomer species. The present disclosure contemplates embodiments of a hybrid collagen-fibril matrix that include collagen building blocks associated with non-collagen molecules within the fibrils of the matrix (referred to herein as "hybrid fibrils") and also embodiments of a hybrid collagen fibril matrix in which the noncollagen molecules polymerize separately from the collagen fibrils to produce separate collagen fibrils and non-collagen polymers within the hybrid collagen-fibril matrix. In another embodiment, a hybrid collagen-fibril matrix is formed by providing a polymerized non-collagen polymer or copolymer defining pores and interstitial spaces, introducing an aqueous fluid comprising soluble collagen-fibril matrix building blocks into the interstitial spaces and polymerizing the building blocks to form a collagen-fibril matrix within the interstitial spaces.

In another aspect, the present disclosure is directed to pre-matrix compositions that are formulated for subsequent polymerization to provide insoluble synthetic collagen-fibril matrices and/or collagen-based therapeutic delivery devices. Polymerization of a pre-matrix composition to form a collagen-fibril matrix, can be accomplished under controlled conditions, wherein the controlled conditions include, but are not limited do, pH, phosphate concentration, temperature, buffer composition, ionic strength, and composition and concentration of the building blocks and other optional molecules present in a given pre-matrix composition, which can include both collagen molecules and non-collagenous molecules.

As used herein, the term "pre-matrix composition" refers to an aqueous fluid that includes soluble collagen-fibril matrix building blocks, the building blocks including oligomers and optionally one or more type of non-oligomeric soluble collagen molecules, which building blocks demonstrate a capacity to self-assemble or polymerize into higher order structures (macromolecular assemblies) in the absence of exogenous cross-linking agents. In one embodiment, the building blocks are selected based on their molecular composition and fibril-forming capacity. In one embodiment, the non-oligomeric soluble collagen molecules include one or both of telocollagen molecules and atelocollagen molecules.

In accordance with an illustrative embodiment of the present disclosure, a pre-matrix composition comprises a collagen polymer solution comprising different types of collagen polymer building blocks, including but not limited to oligomer, monomer/telocollagen (also referred to as telomer) and atelocollagen (also referred to as atelomer). These building blocks, as shown in FIG. 1, differ based on their intermolecular cross-link content, composition and cross-link chemistries. Referring to FIG. 1, (A) depicts an oligomer, (B) telocollagen and (C) an atelocollagen. Gray bars in FIG. 1 represent stable, mature covalent cross-links.

In some embodiments, the building blocks are obtained by solubilizing collagen from tissue and purifying the soluble collagen. For example, the building blocks can be prepared by utilizing acid-solubilized collagen and defined polymerization conditions that are controlled to yield three-dimensional collagen matrices with a range of controlled assembly kinetics (e.g., polymerization half-time), molecular compositions, and fibril microstructure-mechanical properties, for example, as described in U.S. patent application Ser. No. 11/435,635 (published Nov. 22, 2007, as U.S. Publication No. 2007/0269476) and Ser. No. 11/903,326 (granted Dec. 27, 2011, as U.S. Pat. No. 8,084,055), each incorporated herein by reference in its entirety. In one embodiment, the collagen is Type I collagen. In certain aspects of the present disclosure, the collagen-fibril matrix building blocks have been removed from a source tissue. Optionally, the building blocks may be solubilized from the tissue source, while in still other embodiments, the building blocks comprise synthetic collagen. In still other embodiments, the building blocks comprise recombinant collagen.

In any of the various embodiments described herein, the collagen compositions of the present disclosure can be combined, prior to, during, or after polymerization, with nutrients, including minerals, amino acids, sugars, peptides, proteins, vitamins (such as ascorbic acid), or glycoproteins that facilitate hematopoietic stem cell culture, such as laminin and fibronectin, hyaluronic acid, or growth factors such as platelet-derived growth factor, or transforming growth factor beta, and glucocorticoids such as dexamethasone. In other illustrative embodiments, fibrillogenesis inhibitors, such as glycerol, glucose, or polyhydroxylated compounds can be added prior to or during polymerization. In accordance with one embodiment, cells can be added to the collagen or extracellular matrix components as the last step prior to the polymerization or after polymerization of the collagen compositions. In other illustrative embodiments, cross-linking agents, such as carbodiimides, aldehydes, lysyl-oxidase, N-hydroxysuccinimide esters, imidoesters, hydrazides, and maleimides, and the like can be added before, during, or after polymerization.

A variety of techniques can be used to control the therapeutic release profile (also referred to as the molecular release profile) of a collagen-based therapeutic delivery system described herein. In one aspect of this disclosure the pre-matrix composition is modulated to achieve synthetic collagen-fibril materials with a broad range of tunable or customizable fibril microstructures, mechanical properties, and proteolytic degradabilities by the selection of various proportions of oligomeric and non-oligomeric building blocks. The modulation of the synthetic collagen-fiber matrix composition and the self-assembly reaction conditions allow the fibril microstructure and associated interstitial fluid viscosity, mechanical properties and proteolytic degradation to be regulated. The design specificity of the synthetic collagen-fibril matrix allows for the selection of mechanophysical constraints and bioinstructive capacity.

In certain aspects of the therapeutic delivery devices, the collagen-fibril matrix may be tuned such that the predetermined oligomer:non-oligomeric soluble collagen molecule ratio supports burst release, sustained release or variable release of the active agent. Burst release is a rapid release of the active agent within a short timeframe that delivers a bolus type amount of the agent to the target area. Sustained release provides an ongoing release of the active agent at a steady rate for a predetermined period of time. It is envisioned that a therapeutic delivery system can be formulated to provide an early phase, medium phase or late phase burst release of an active agent. It is further recognized that different active agents or different concentrations of an active agent may be released in different phases. It is also recognized that a first active agent may be released in a sustained release while a second active agent may be released in a burst release.

In certain aspects, the therapeutic delivery device comprises more than one layer of synthetic collagen-fibril matrix, each being distinguished by at least one physical property or active agent. The layers may be generated, for example in a spherical fashion, a cylindrical fashion, a planar fashion or other three-dimensional fashion where one layer of synthetic collagen-fibril matrix is completely or almost completely surrounded by at least a second layer of synthetic collagen-fibril matrix, wherein the second layer of collagen matrix comprises at least one different physical property or active agent from the first collagen-fibril matrix layer. Further the collagen-fibril matrix layers may differ by selection of a predetermined oligomer:non-oligomeric soluble collagen molecule ratio, by selection of different active agents, or by different concentrations of the active agent. In another embodiment, the therapeutic delivery device comprises gradients of one or more of physical properties, soluble collagen molecules and active agents.

In addition, following formation of a synthetic collagen-fibril matrix by polymerization, the matrix can be further processed, for example by unconfined or confined compression, to achieve higher-density materials with tissue-like consistency, handling and mechanical properties. Examples of compression processing options are described in U.S. Published Application No. 2015/0105323, the contents of which are hereby incorporated herein by reference.

In accordance with certain aspects of the present disclosure, a synthetic collagen-fibril matrix may be compressed to form a gradient of at least one physical property. As used herein, the term "compressed" can refer to a reduction in size or an increase in density when a force is applied to the collagen-fibril matrix. For example, compression can be achieved through various methods of applying force, such as, but not limited to, confined compression, variable compression, physical compression, centrifugation, ultracentrifugation, evaporation or aspiration. Moreover, in accordance with certain illustrative aspects herein, it should be understood and appreciated that compressing the collagen-fibril matrix can form a gradient of at least one physical property in the composition. As used herein, the term "physical property" can refer to any property of the collagen compositions, including structural, mechanical, chemical, and kinetic properties.

In accordance with certain embodiments, the gradient is a compression-induced gradient. As used herein, the phrase "compression-induced gradient" refers to a gradient in the collagen-fibril matrix that is provided as a result of the compression to which the collagen-fibril matrix is subjected.

In some embodiments, the compression is a physical compression. As used herein, the phrase "physical compression" refers to compression of a collagen-fibril matrix by applying force by physical means.

In other embodiments, the compression is a confined compression. As used herein, the phrase "confined compression" refers to confinement of the collagen-fibril matrix as it undergoes compression.

In yet other embodiments, the compression is a variable compression. As used herein, the phrase "variable compression" refers to compression of a collagen-fibril matrix by applying force in a non-linear fashion.

In still other embodiments, the compression is centrifugation. In some embodiments, the compression is ultracentrifugation. In yet other embodiments, the compression is evaporation. In some embodiments, the compression is aspiration. In certain embodiments, the aspiration is vacuum aspiration. In select embodiments, the compression is not plastic compression because such plastic compression may be an extreme process in which nearly all of the fluid removable from collagen compositions is excreted, and can reduce the cellular viability of the scaffolds and damage the natural matrix architecture.

For embodiments in which the compression is a physical compression, the physical compression can be performed in a chamber comprising an adjustable mold and platen. Typically, collagen-fibril matrix can be inserted into the mold and then subjected to compression.

Furthermore, the physical compression can be varied depending on the placement of the porous platen within the mold. For example, the mold may be adjustable so that porous polyethylene is positioned as part of the platen and/or along the walls or bottom of the sample mold. The location of the porous polyethylene can define the resultant material gradient in the collagen-fibril matrix. In some embodiments, the compression is a physical force from at least one direction. In other embodiments, the compression is a physical force from two or more directions. In yet other embodiments, the compression is a physical force from three or more directions. In some embodiments, the compression is a physical force from four or more directions.

Pursuant to certain aspects of the present disclosure, a synthetic collagen-fibril matrix as described herein may be made under controlled conditions to obtain particular physical properties. For example, the collagen-fibril matrices may have desired collagen fibril density, pore size (fibril-fibril branching), elastic modulus, tensile strain, tensile stress, linear modulus, compressive modulus, loss modulus, fibril area fraction, fibril volume fraction, collagen concentration, cell seeding density, shear storage modulus (G' or elastic (solid-like) behavior), and phase angle delta ($\delta$ or the measure of the fluid (viscous)- to solid (elastic)-like behavior; $\delta$ equals 0° for Hookean solid and 90° for Newtonian fluid).

As used herein, a "modulus" can be an elastic or linear modulus (defined by the slope of the linear region of the stress-strain curve obtained using conventional mechanical testing protocols; i.e., stiffness), a compressive modulus, a loss modulus, or a shear storage modulus (e.g., a storage modulus). These terms are well-known to those skilled in the art. As used herein, a "fibril volume fraction" (i.e., fibril density) is defined as the percent area of the total area occupied by fibrils in three dimensions.

A collagen-based therapeutic delivery device as described herein can be formed for subsequent implantation into a patient, such as, for example, as a tissue graft material, or can be formed in situ by injecting a pre-matrix composition to a location in situ for subsequent polymerization to form a collagen-based therapeutic delivery material in situ.

In some embodiments, the collagen-based therapeutic delivery device is a medical graft. An important consideration for medical grafts, particularly soft tissue grafts is the design of a graft that promotes graft vascularization, and particularly one that allows for cell co-implantation and cell infiltration, that structurally and functionally supports cell growth, and that is able to fully integrate with the tissue physiologically. Additional important considerations include that the graft should not impede the growth of regenerating tissue and that its degradation should not leave behind any byproducts that would adversely affect the cells involved in tissue regeneration. The collagen-based therapeutic delivery systems described herein not only allow for cell co-implantation and cell infiltration, structurally and functionally supports cell growth, and are able to fully integrate with the tissue physiologically by providing a strong porous framework suitable for cell infiltration and growth, but they also enable the delivery of vascularization-promoting active agents to the site of the graft to enhance vascularization following implant. The collagen-fibril matrix can be formed in any two- or three-dimensional shape by conducting polymerization in a mold having a desired shape and size and/or by post-polymerization processing.

In other embodiments, the collagen-based therapeutic delivery system can be used in vitro. For example, in vitro use of the collagen-based therapeutic delivery systems of the present disclosure may be utilized for research purposes such as cell tissue culture, drug discovery, and chemical toxicity testing. In other embodiments, the collagen-based therapeutic delivery system can be used in vitro for generating complex tissue and organ constructs, including vascularization, for restoration of damaged or dysfunctional organs or tissues.

In accordance with certain aspects herein, the collagen-fibril matrices may include, but are not limited to, low density fibril matrices and high density fibril matrices. A low density fibril matrix may have a collagen concentration less than about 10 mg/ml, 9 mg/ml, 8 mg/ml, 7 mg/ml, 6 mg/ml, 5 mg/ml, 4 mg/ml, 3 mg/ml, 2 mg/ml or 1 mg/ml. A high density fibril matrix may have a collagen concentration greater than 10 mg/ml, 20 mg/ml, 30 mg/ml, and 40 mg/ml or higher. Applications suitable for low density fibril matrices may include, but are not limited to, in vitro 3D cell culture, injectable therapeutic delivery, and implantable therapeutic delivery. Applications suitable for high density fibril matrices or tissue constructs may include, but are not limited to, surgical implants, sheets, fibrillar material, tissue valves, tissue gradients, articular cartilage and tissue-engineered medical products.

It should be understood and appreciated herein that the illustrative collagen-based therapeutic delivery systems of the present disclosure can be used in human and veterinary medicine in both experimental and in vivo conditions. Envisioned uses of the illustrative therapeutic delivery systems in accordance with the teachings of the present disclosure include, but are not limited to, as hemostatic agents, as missing tissue substitutes or replacements, as skin equivalents, and as matrices for tissue augmentation. The desired physical characteristics of the collagen-fiber matrix for use in different applications may differ depending on the application and the active agent.

Various examples demonstrating preparation and testing of compositions, processes and methods of the present disclosure are described in the following examples. These examples are illustrative only and are not intended to limit or preclude other embodiments of the present disclosure. Moreover, it should be understood and appreciated herein that in order to measure and compare molecular release kinetics from various collagen-fibril materials in the presence and absence of collagenase, an in vitro model system was designed to measure release kinetics from collagen fibril materials by subjecting the polymerized 3D collagen matrix system with admixed FITC-Dextran molecules to collagenase or 1×PBS. In particular, the in vitro model system involved admixing of FITC-Dextrans of various sizes ranging from 10 kDa to 2 MDa within polymerizable collagens, and then establishing a computational model to predict release kinetics for various sized molecules based on known diffusion coefficients for oligomer matrices. The designed experimental model system was then used to define and compare size-dependent molecular release kinetics for FITC-Dextrans within low-density matrices prepared with standardized collagen oligomers and commercial monomeric collagen.

As used herein, the term "mammalian" refers to any species belonging to the class Mammalia including, but not limited to, humans, cows, pigs, dogs, horses or cats.

As used herein, the term "mammalian tissue" refers to any tissue including, but not limited to, skin, muscle, tendons or fibrous connecting tissue found in mammals.

As used herein, the term "diffusion" refers to the random thermal motion of atoms, molecules, clusters of atoms, etc. in gases, liquids, and some solids.

As used herein, the term "fibrillogenesis" refers to the process of tropocollagen monomers assembling into mature fibrils and associated fibril-network structures.

As used herein, the term "gel" refers to a three-dimensional network structure arising from intermolecular polymer chain interactions.

As used herein, the term "permeability" refers to a measure of the ability of porous materials to transmit fluids; the rate of flow of a liquid through porous material.

As used herein, the term "recombinant collagen protein/peptide" refers to a collagen or collagen-like polypeptide produced by recombinant methods, such as, but not limited to by expression of a nucleotide sequence encoding, the protein or peptide in a microorganism, insect, plant or animal host. Such compositions often comprise Gly-X-Y triplets where Gly is the amino acid glycine and X and Y can be the same or different, are often proline or hydroxyproline, but can be any known amino acid.

As used herein, the term "self-assembly" refers to the process by which a complex macromolecule (for example collagen) or a supramolecular system (for example a virus) spontaneously assembles itself from its components.

As used herein, the term "solution" refers to a type of homogenous mixture composed of only one phase. In such a mixture a "solute" is a substance dissolved in another substance, known as a "solvent".

As used herein, the term "stiffness" is a general term describing the extent to which a material resists deformation in response to an applied force; specific measures of stiffness depend upon the material loading format (for example, tension, compression, shear, bending).

As used herein, the term "degradation" refers to a change in chemical, physical or molecular structure or appearance (for example, gross morphology) of material; degradation of collagen under physiological conditions involves site-specific cleavage within the central triple helical region by proteolytic enzymes known as collagenases. Collagenases are members of the larger family of proteases known as matrix metalloproteases.

As used herein, the term "solubility" refers to a measure of the extent to which a material can be dissolved; in the context of collagen polymers, solubility refers to collagen molecules (partial, full or multiples) or peptides in a solution; further qualification of solubility may include "acid-soluble" and "neutral salt-soluble" which describe compositions that are soluble in dilute acids and neutral salt solutions, respectively.

As will be appreciated from the above descriptions, taken together with the Examples provided below, the present specification discloses a wide variety of forms and embodiments, some examples of which are described as follows:

In one form, the present disclosure provides a collagen-based therapeutic delivery device that includes an insoluble synthetic collagen-fibril matrix comprising a polymerization product of soluble oligomeric collagen or a polymerization product of a mixture of soluble oligomeric collagen with one or more type of non-oligomeric soluble collagen molecules; and a first active agent dispersed throughout the collagen-fibril matrix or within a portion of the collagen-fibril matrix. Also provided are the following embodiments:

(1) Any of the embodiments disclosed herein wherein the collagen-fibril matrix exhibits a stiffness of at least 5 Pa.

(2) Any of the embodiments disclosed herein wherein the collagen-fibril matrix comprises type I collagen.

(3) Any of the embodiments disclosed herein wherein the one or more other type of non-oligomeric soluble collagen molecules comprises one or both of soluble telocollagen molecules and soluble atelocollagen molecules.

(4) Any of the embodiments disclosed herein wherein the collagen-based therapeutic delivery device is a tissue graft.

(5) Any of the embodiments disclosed herein wherein the collagen-based therapeutic delivery device is lyophilized.

(6) Any of the embodiments disclosed herein wherein the collagen-fibril matrix comprises a polymerization product of a mixture of soluble oligomeric collagen with one or more type of non-oligomeric soluble collagen molecules and wherein the oligomeric collagen and non-oligomeric soluble collagen molecules are in a ratio within a range selected from the group consisting of 0:100 to 5:95, 5:95 to 10:90, 10:90 to 15:85, 15:85 to 20:80, 20:80 to 25:75, 25:75 to 50:50, 50:50 to 75:25 and 75:25 to 100:0.

(7) Any of the embodiments disclosed herein, further comprising a second active agent dispersed throughout the collagen-fibril matrix or within a portion of the collagen-fibril matrix.

(8) Any of the embodiments disclosed herein wherein each of the first and second active agents is a growth factor or a drug.

(9) Any of the embodiments disclosed herein wherein the collagen-fibril matrix includes a first portion having a first density and a second portion having a second density; wherein the first density is different than the second density.

(10) Any of the embodiments disclosed herein wherein the collagen-fibril matrix includes a first portion having dispersed therein the first active agent and a second portion having dispersed therein a second active agent, wherein the therapeutic delivery device exhibits a first release profile for the first active agent and a second release profile for the second active agent, and wherein the first release profile is different than the second release profile.

In another form, the present disclosure provides a method for making a therapeutic delivery device that includes (i) forming an aqueous solution comprising a first quantity of soluble collagen-fibril building blocks; (ii) causing the building blocks to polymerize by self-assembly, thereby forming an insoluble synthetic collagen-fibril matrix; and (iii) either (a) including a second quantity of an active agent in the aqueous solution whereby said causing forms the insoluble synthetic collagen-fibril matrix having the active agent dispersed therein or (b) contacting the insoluble synthetic collagen-fibril matrix with the second quantity of the active agent to form a collagen-fibril matrix having the active agent dispersed therein; wherein the first quantity of building blocks comprises soluble oligomeric collagen molecules. Also provided are the following embodiments:

(1) Any of the embodiments disclosed herein wherein the collagen-fibril matrix exhibits a stiffness of at least 5 Pa.

(2) Any of the embodiments disclosed herein wherein the first quantity of building blocks further comprises soluble non-oligomeric collagen molecules.

(3) Any of the embodiments disclosed herein, further comprising compressing the insoluble synthetic collagen-fibril matrix to form a condensed insoluble synthetic collagen-fibril matrix.

(4) Any of the embodiments disclosed herein wherein said compressing comprises subjecting the insoluble synthetic collagen-fibril matrix to confined compression.

(5) Any of the embodiments disclosed herein, further comprising, after said causing, lyophilizing the insoluble synthetic collagen-fibril matrix.

In still another form, the present disclosure provides a pre-matrix composition that comprises an aqueous solution including a first quantity of soluble collagen-fibril building blocks and a second quantity of an active agent in the aqueous solution, wherein the first quantity of soluble collagen-fibril building blocks includes soluble oligomeric collagen or a mixture of soluble oligomeric collagen with one or more other type of non-oligomeric soluble collagen molecules, wherein the building blocks are operable to self-assemble into a macromolecular insoluble synthetic collagen-fibril matrix having a stiffness of at least 5 Pa in the absence of an exogenous cross-linking agent. Also provided are the following embodiments:

(1) Any of the embodiments disclosed herein wherein the one or more other type of non-oligomeric soluble collagen molecules comprises one or both of soluble telocollagen molecules and soluble atelocollagen molecules.

(2) Any of the embodiments disclosed herein wherein the oligomeric collagen comprises type I collagen.

(3) Any of the embodiments disclosed herein wherein the active agent is a growth factor or a drug.

(4) Any of the embodiments disclosed herein wherein the active agent is covalently attached to one or more of the building blocks.

(5) Any of the embodiments disclosed herein wherein the pre-matrix composition comprises the oligomeric collagen and non-oligomeric soluble collagen molecules in a ratio within a range selected from the group consisting of 0:100 to 5:95, 5:95 to 10:90, 10:90 to 15:85, 15:85 to 20:80, 20:80 to 25:75, 25:75 to 50:50, 50:50 to 75:25 and 75:25 to 100:0.

(6) Any of the embodiments disclosed herein wherein the pre-matrix composition is capable of being modulated to achieve a nonsoluble synthetic collagen-fibril matrix that exhibits an optimized active agent release profile for the active agent.

In yet another form, the present disclosure provides a method for delivering an active agent, that includes positioning at an in situ position (i) a pre-matrix composition comprising an aqueous solution including a first quantity of soluble collagen-fibril building blocks and a second quantity of an active agent in the aqueous solution, wherein the first quantity of soluble collagen-fibril building blocks includes soluble oligomeric collagen or a mixture of soluble oligomeric collagen with one or more type of soluble non-oligomeric collagen molecules, wherein the building blocks are operable to self-assemble into an insoluble synthetic macromolecular collagen-fibril matrix having a stiffness of at least 5 Pa in situ in the absence of an exogenous cross-linking agent; or (ii) a collagen-based therapeutic delivery device comprising an insoluble synthetic collagen-fibril matrix comprising a polymerization product of soluble oligomeric collagen or a polymerization product of a mixture of soluble oligomeric collagen with one or more type of soluble non-oligomeric collagen molecules; and a first active agent dispersed throughout the collagen-fibril matrix or within a portion of the collagen-fibril matrix; wherein the collagen-fibril matrix exhibits a stiffness of at least 5 Pa.

EXAMPLE 1

Formulation of Collagen-Fibril Delivery Devices

Soluble collagen-fibril building blocks including oligomer, telocollagen, and atelocollagen (or oligomer, telomer, and atelomer) were derived from the dermis of market weight pigs. Oligomer formulations were prepared using an acid solubilization method that preferentially extracts oligomers, which represent aggregates of collagen molecules (e.g., trimer) covalently connected by a natural intermolecular crosslink. Telomer formulations were prepared using acid solubilization followed by a salt precipitation technique. Salt solutions were used to selectively isolate collagen molecules, which were not cross-linked or which contained immature acid labile cross-links, particularly since telomer and oligomer formulations contain reactive aldehyde groups on the telopeptide ends. Finally, atelocollagen formulations were prepared through a digestion technique in which pepsin enzymatically cleaves the telopeptide ends from the N- and C-terminus of the collagen molecule. These soluble collagen-fibril building blocks are standardized and quality controlled based upon their molecular composition and polymerization (collagen-fibril formation) capacity. For comparison to commercial grade collagen, acid solubilized type I collagen harvested from rat tails was purchased from BD Biosciences (Bedford, Mass., referenced as BD-rat tail collagen, BD-RTC).

Figure 2:
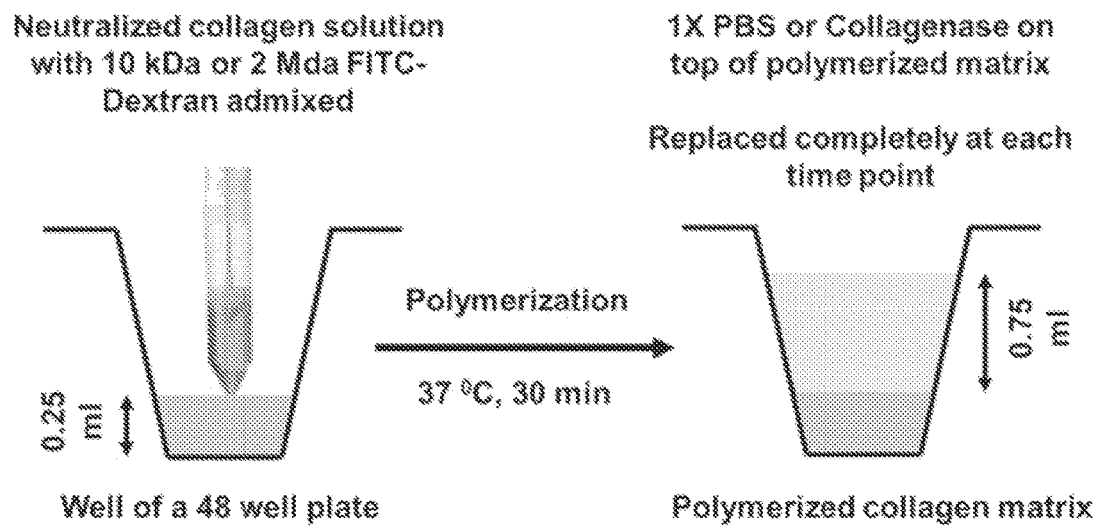
FIG. 2 depicts an illustrative representation of the formation a collagen matrix-based delivery system in a well of a 48 well plate as described in Example 1 of the present disclosure, and wherein the delivery device, in turn, is placed in a reservoir of phosphate buffered saline (PBS) in the presence or absence of collagenase to measure experimentally its agent release profile.

For preparation of collagen-fibril delivery devices from various acid solubilized collagen solutions, the collagens were further diluted in 0.01N HCl and further neutralized with phosphate buffered saline (PBS, 10×, pH 7.4) and 0.1N sodium hydroxide (NaOH) to achieve neutral pH (7.4) and a final collagen concentration of 3 mg/ml. For formulating matrices with molecules admixed freely in it, FITC-Dextran of four different sizes (i.e., 10, 40, 500 and 2 MDa) were loaded to mimic different sized therapeutic molecules. Here, FITC-Dextrans (10 kDa, 40 kDa, 500 kDa, or 2 MDa, from Invitrogen, Eugene, Oreg.) were solubilized in 10×PBS to yield desired final concentration within polymerized matrices. FITC-Dextran enables straightforward quantification of release kinetics based on fluorescence level detection from supernatant above collagen matrix system. All the neutralized solutions were polymerized in 0.25 ml volume in a 48 well plate (Corning, USA), as shown in FIG. 2. The system allowed molecular release kinetics into 0.75 ml top buffer which was 1×PBS (pH 7.4) in the absence or presence of collagenase (type IV, from Worthington Biochemical Corporation, USA).

EXAMPLE 2

Admixing FITC-Dextran has No Effect on Collagen-fibril Polymerization Kinetics or Collagen-fibril Matrix Visco-elastic Properties To confirm that the addition of FITC-Dextran had no effect on collagen-fibril polymerization kinetics and collagen-fibril delivery device physical properties, oligomer matrices (3 mg/ml) were neutralized in the absence and presence of FITC-Dextrans (10 KDa and 2 MDa, each at a final concentration of 1.0 mg/ml) as described in procedure above. Each neutralized solution was put on AR2000 rheometer adapted with a stainless steel 40 mm diameter parallel plate geometry (TA Instruments, New Castle, Del.) for polymerization in contact with the steel plate. Time-dependent changes in viscoelastic properties (shear storage modulus (G'), shear loss modulus (G"), and tan of phase shift delta (δ)) during polymerization were monitored through oscillatory shear, using a time sweep procedure. Temperature of the rheometer plate was maintained at 4° C. for a period of 5 minutes to get the baseline of storage modulus of neutralized collagen solutions with or without FITC-Dextran prior to polymerization. The temperature was then increased to 37° C. to induce polymerization of matrices. Polymerization kinetics and viscoelastic properties of matrices prepared with or without FITC-Dextran were compared. Polymerization half time (Thalf) was calculated along with the rate of polymerization, defined as the slope of polymerization curve for each sample. Each formulation was tested in triplicate.

Figure 3:
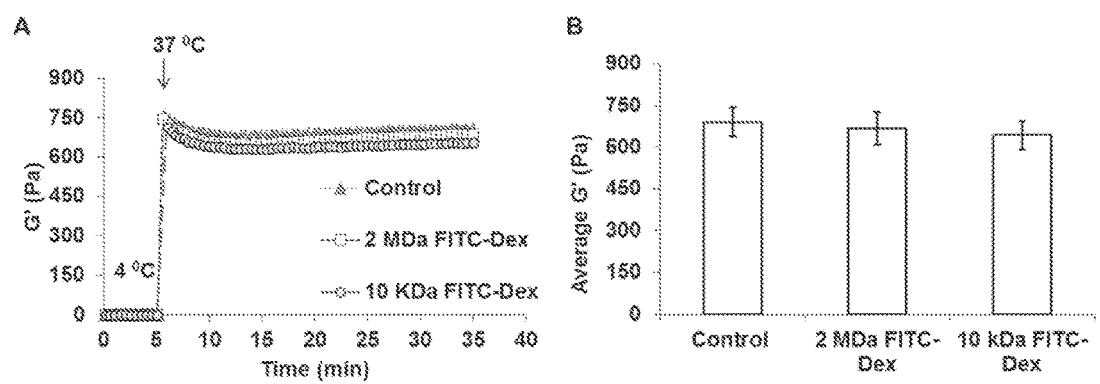
FIG. 3 depicts a graphical representation of the effect of admixed FITC-Dextrans (2 mg/ml) on the collagen-fibril polymerization kinetics (A) and physical properties (B) of the collagen-fibril matrix delivery device as described in Example 2 of the present disclosure.

Results indicated that admixing FITC-Dextrans at 1 mg/ml did not significantly affect collagen-fibril polymerization kinetics or the viscoelastic properties for the resultant collagen-fibril matrix (p>0.05), as shown in FIG. 3. In particular, FIG. 3A shows polymerization kinetics as measured by time-dependent changes in G', while FIG. 3B shows associated final G' values for 3 mg/ml oligomer matrices prepared in absence and presence of 10 KDa and 2000 KDa FITC-Dextrans (1 mg/ml).

EXAMPLE 3

Predicting Time Required for Diffusion-based Release of Various Sized FITC-Dextran Molecules from Collagen-fibril Materials To predict the diffusion-based release kinetics of various sized FITC-Dextrans from collagen-fibril matrices as well as define reservoir sampling times, an established mathematical model for monolithic matrices was adapted. The mathematical model was based on Fick's second law of diffusion for a slab matrix geometry with homogeneous initial drug distribution within the collagen matrix system and an associated supernatant "sink."

Equations used for predictive modeling of short-time and long-time release were:
Short-time:

$$\frac{M_t}{M_\infty} = 4\left(\frac{Dt}{\pi L^2}\right)^{\frac{1}{2}}$$

Long-time:

$$\frac{M_t}{M_\infty} = 1 - \frac{8}{\pi^2}\exp\left(-\frac{\pi^2 Dt}{L^2}\right)$$

Here, $M_t$ and $M_\infty$ denote the cumulative amounts of drug released at time t and at infinite time respectively; D is the diffusion coefficient of the drug within the system, and L represents the total thickness of the matrix. Length values for collagen-fibril matrices were 2.61 mm as defined by our experimental system. Diffusion coefficient values (D) used for 10 KDa, 40 KDa, 500 KDa and 2 MDa FITC-Dextrans were 1.09 E-10, 4.8 E-11, 2.52 E-11, and 1.76 E-11 (m$^2$/sec) based upon previous published values for 3 mg/ml oligomeric collagen matrices.

Figure 4:
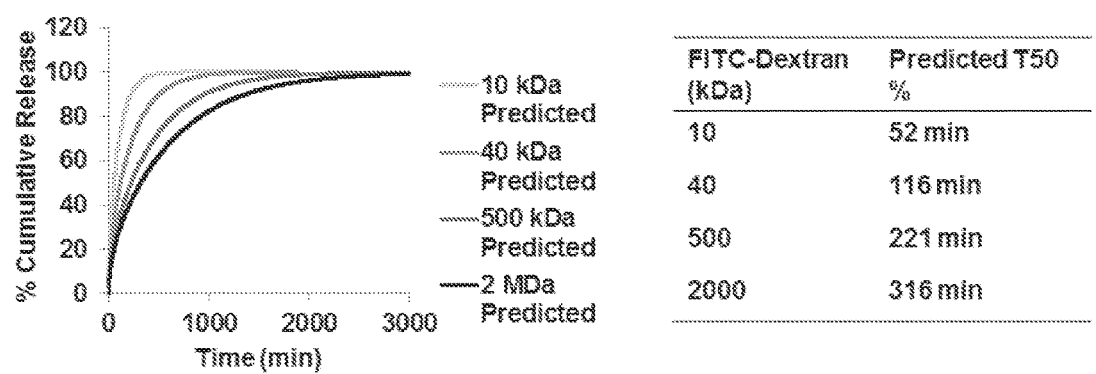
FIG. 4 depicts an illustrative representation of size-dependent molecular release kinetics as predicted using a diffusion-based mathematical model as described in Example 3.

Results obtained showed that release rates decreased while T50% of release (Time required for 50% of cumulative release) increased as the FITC-dextran size increased, as demonstrated in FIG. 4. Such size-dependent release kinetics might be expected as the diffusion coefficient (D) of FITC-Dextrans decreases with increasing molecular size.

EXAMPLE 4

Comparison of Size-dependent Molecular Release Kinetics for Low-density (3 mg/ml) Oligomer and Commercial Monomer Collagen-fibril Matrices in the Presence and Absence of Collagenase To further validate and demonstrate the utility of the designed experimental model for defining molecular release kinetics of collagen-fibril matrices, 10 KDa, 40 KDa, 500 KDa and 2 MDa FITC-Dextrans were admixed in oligomer and commercial monomer matrices and their release was compared from the designed in vitro experimental model system. Matrices (250 µl each) were prepared in 48 well pates with 750 µl reservoir of PBS (1×, pH 7.4) on top to induce diffusion-based release. To simulate release kinetics based on both diffusion and proteolytic degradation of collagen-matrices, a subset of experiments were conducted in the presence of 125 U/ml collagenase from *Clostridium Histolyticum* (Worthington Biochem Corporation, USA). It should be noted that the reservoir buffer choice made in accordance with the present system allowed the following to be investigated 1) the effect of collagen microstructure alone on molecular release, when 1×PBS was used (absence of collagenase condition); and 2) the effect of collagen microstructure along with its proteolytic degradability on molecular release, when 125 U/ml collagenase was used (presence of collagenase condition).

Figure 15:
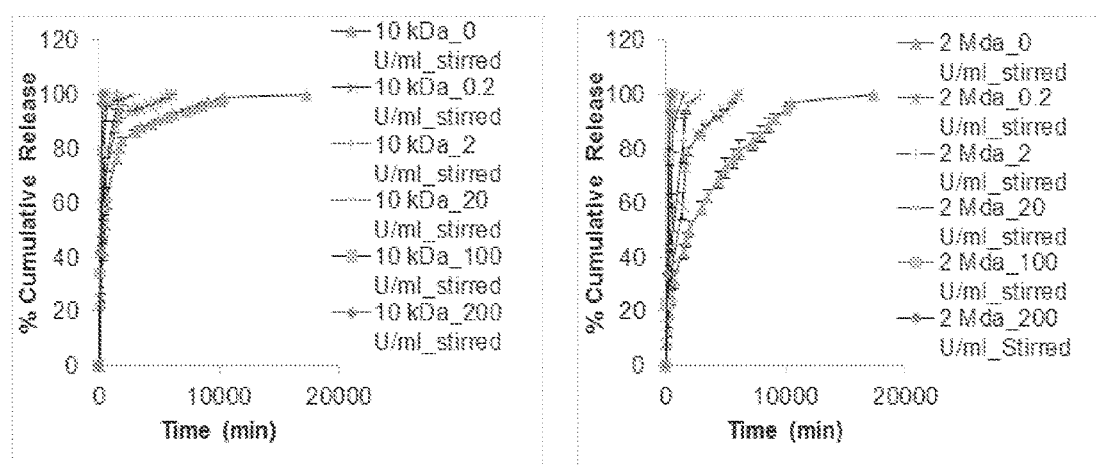
FIG. 15 represents release kinetics data obtained from low-density (3 mg/ml) oligomer matrices prepared with either 10 kDa (left panel) or 2 MDa (right panel) FITC-Dextran and treated with the indicated collagenase concentration as described in Example 4 of the present disclosure.
Figure 16:
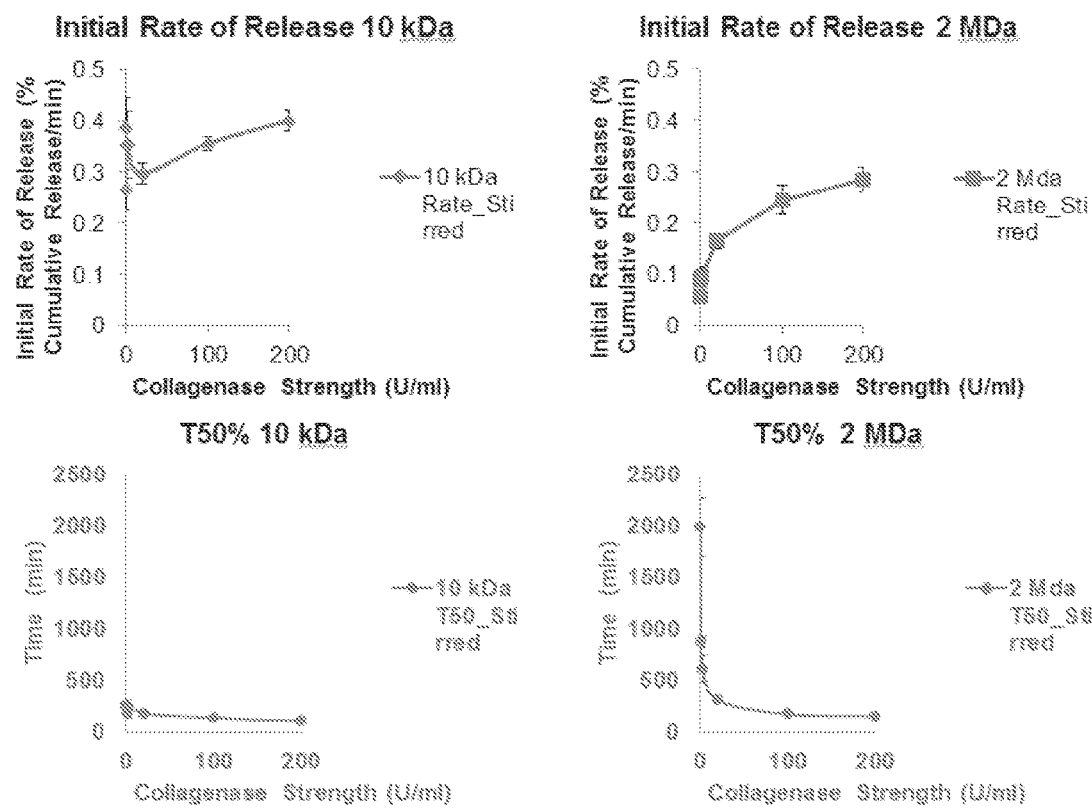
FIG. 16 depicts illustrative graphs showing the initial rates of release and T50% curves calculated from the release kinetics curves of FIG. 15 for the various collagenase concentrations.

At various time points, the supernatant was removed and replaced with fresh PBS or collagenase according to the system. FITC-dextran within the supernatant then was determined spectrofluorometrically (Molecular Devices Spectramax M5) at excitation and emission wavelengths of 493 and 530 nm, respectively. This process was repeated until Relative Fluorescence Units from supernatant of wells matched baseline fluorescence (PBS plus/minus collagenase containing no FITC-Dextran), indicating completion of the FITC-Dextran release. All fluorescence values were normalized to maximum total fluorescence intensity and % cumulative release was plotted versus time. Additional effects of collagenase levels on release kinetic curves for 10 KDa and 2 MDa FITC-Dextran can be seen in the graphical representation of FIG. 15. In particular, low-density polymerized oligomer matrices (3 mg/ml) containing 10 KDa or 2 MDa FITC-dextran were subjected to various collagenase levels and release kinetics measured. In addition, FIG. 16 depicts illustrative graphs showing the initial rates of release and T50% curves calculated from the release kinetics curves for the various collagenase concentrations.

Figure 5:
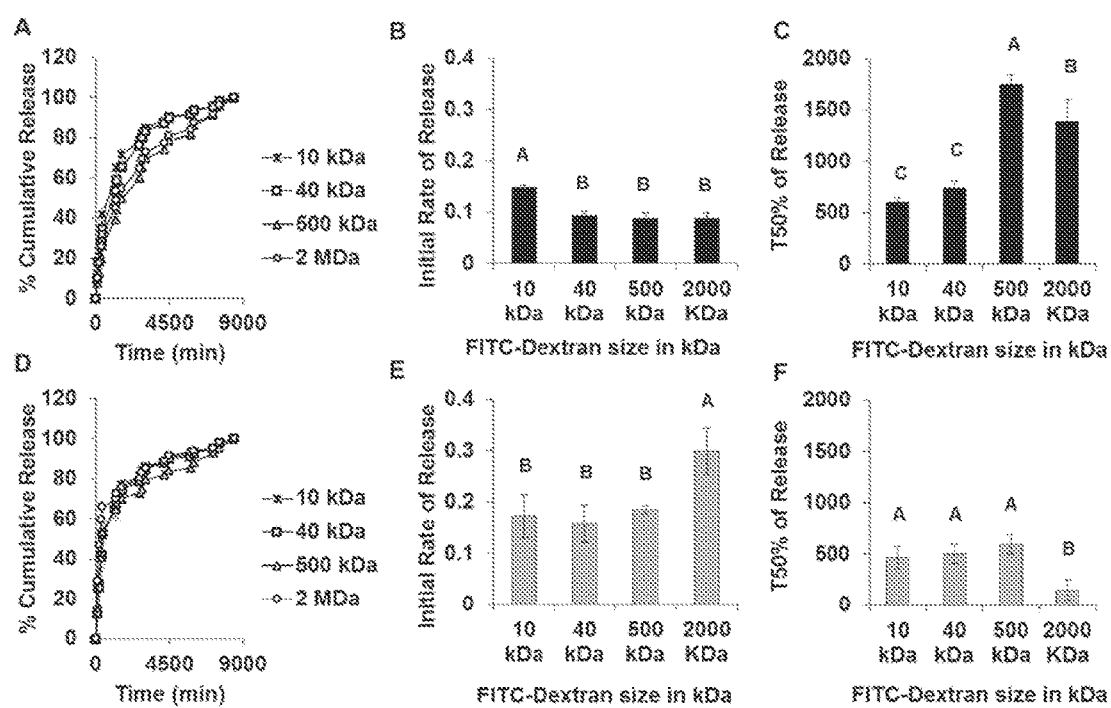
FIG. 5 represents data obtained from analyzing the molecular release of polymerizable oligomer collagen and commercial monomer collagen (BD rat tail) matrices as described in Example 4 of the present disclosure.

Referring now to FIG. 5, size dependent molecular release was observed with polymerizable oligomer matrices but not commercial BD rat tail matrices. More particularly, FITC-Dextrans with molecular sizes of 10 kDa (X), 40 kDa (□), 500 kDa (Δ), and 2 MDa (○) were polymerized at 0.5 mg/ml within oligomer and commercial monomer (BD rat tail) matrices (3 mg/ml). For oligomer (A) and commercial monomer (D) collagen matrices, time-dependent release profiles were monitored spectrofluorometrically, and initial release rate (mean±SD; n=3; B,E) and T50% (mean±SD; n=3; C,F) quantified. For each panel, letters indicate statistically different experimental groups as determined by Tukey-Kramer range test (p<0.05). When 1×PBS buffer was used to investigate effect of collagen microstructure on molecular release, results showed that oligomer matrices showed release profiles that were dependent on the size of FITC-Dextrans (FIG. 5A). In contrast, such size dependent molecular release was not observed with commercial monomer matrices prepared at the same concentration (FIG. 5D). The quantification of initial release rates from oligomer (B) showed a trend of decreasing release rate as FITC-Dextran size became larger (10 KDa to 2 MDa) and an increasing trend for T50% (C). These trends were consistent with those predicted by the computational model. No such size-dependent trends were observed in the release rates or T50% for commercial monomer matrices. The results showed that the microstructure of oligomer collagen-fibril matrices provided improved control of FITC-Dextran release kinetics, compared to that of commercial BD rat tail collagen monomer matrices.

Figure 6:
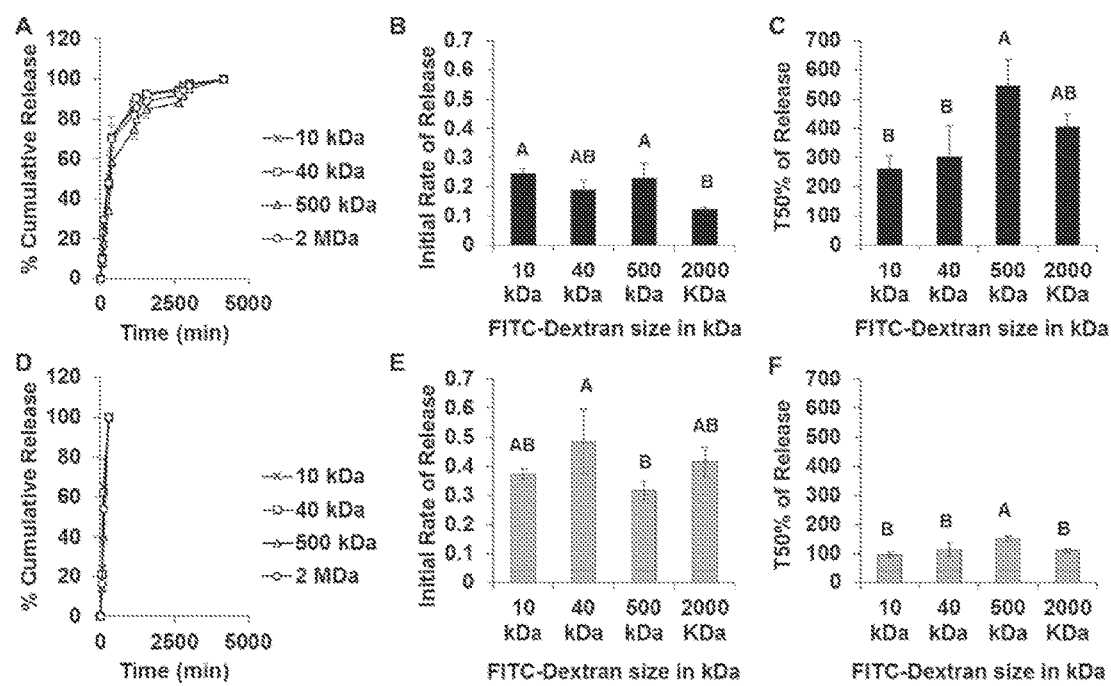
FIG. 6 represents data obtained from analyzing the molecular release of oligomer collagen-fibril compositions and commercial monomer collagen-fibril matrices in the presence of collagenase as described in Example 4 of the present disclosure.

Referring to FIG. 6, oligomer matrices in the presence of collagenase were found to maintain size dependent and sustained release trends, while commercial monomer (BD rat tail) matrices did not. In particular, FITC-Dextrans with molecular sizes of 10 kDa (X), 40 kDa (□), 500 kDa (Δ), and 2 MDa (○) were polymerized at 0.5 mg/ml within oligomer and commercial monomer matrices (3 mg/ml). For oligomer (A) and commercial monomer (D) matrices, time-dependent release profiles were monitored spectrofluorometrically in the presence of collagenase (125 U/ml), and initial release rate (mean±SD; n=3; B,E) and T50% (mean±SD; n=3; C,F) were quantified. For each panel, letters indicate statistically different experimental groups as determined by Tukey-Kramer range test (p<0.05). When 125 U/ml collagenase was used to investigate the effect of proteolytic degradability in addition to collagen microstructure on the FITC-Dextran release kinetics, oligomer matrices maintained size dependent and sustained release profiles (FIG. 6A), while commercial monomer collagen matrices showed more rapid "burst" release for all molecular sizes tested for a given time period (FIG. 6 D). The quantification of initial slopes of release profiles gave significantly higher rates of release and significantly lesser T50% for commercial monomer matrices compared to the oligomer matrices (p<0.05), indicating the rapid proteolytic degradability and inability of commercial monomer matrices to support molecular release for extended period of time.

Thus, results indicated successful formation of a multifunctional biograft material that was experimentally tested for release of various sized FITC-Dextran molecules in vitro. The designed experimental model allowed the effect of the collagen-fibril microstructure to be investigated alone, as well as both collagen-fibril microstructure and proteolytic degradability on molecular release.

After establishing the functionality and robustness of the illustrative collagen-fibril matrix system for delivery of different sizes of FITC-Dextran molecules, the collagen biograft system can then be modulated to make it tunable for release. It should be understood and appreciated herein that molecular release can be affected by two key parameters, namely 1) the collagen fibril microstructure, and 2) its proteolytic degradability. As such, it was an objective to incorporate approaches for modulating these two parameters to customize release kinetics from collagen-fibril materials. It was believed that by using different interfibril branching capacity of collagen building blocks and by altering the collagen fibril density, molecular release kinetics at suprafibrillar level of assembly can be tuned.

It was proposed to characterize molecular release from low-density (3 mg/ml) collagen-fibril materials, and then to modulate molecular release from these collagen-fibril materials by combining two types of building blocks in collagen-fibril matrices. Thereafter, it was proposed to increase collagen fibril-density to provide the molecular release for extended periods of time and to characterize release from these high-density materials. To further modulate molecular release from these high-density collagen-fibril materials, it was proposed to combine oligomer and telocollagen; and oligomer and atelocollagen blocks in different ratios as a means to modulate proteolytic degradability.

In terms of characterizing molecular release from low-density collagen-fibril materials, it should be understood and appreciated herein that collagen precursors, telocollagens, oligomers and atelocollagens, differ in their intermolecular cross-link composition. It has been previously shown that collagen precursors provide independent control of mechanical and transport properties of collagen matrix. As such, it is therefore hypothesized that the matrices formed from these precursors would exhibit different release kinetics based on their varying fibril microstructure, as well as varying proteolytic degradability, at a matched concentration. In order to test this, proteolytic degradability of matrices were first studied, followed by characterization of molecular release from them in both absence and presence of collagenase. It was also proposed to confirm the effect of microstructure and proteolytic degradability on the release mechanism of matrices by fitting a Weibull function to the molecular release data.

Figure 7:
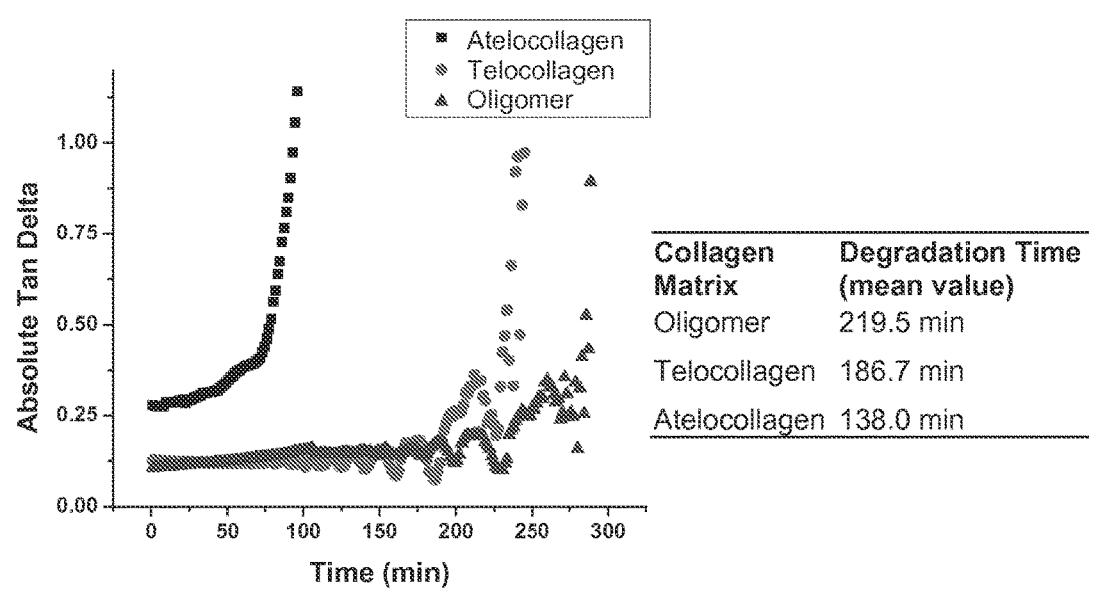
FIG. 7 represents data obtained from an oscillatory shear-based, and strain-controlled time sweep experiment with polymerized atelocollagen (squares), telocollagen (circles) or oligomer (triangles) matrices exposed to 5000 U/ml collagenase as described in Example 4 of the present disclosure.

In order to confirm the proteolytic degradability differences of oligomer vs. telocollagen and atelocollagen matrices, an experiment was performed in which 3 mg/ml oligomer, telocollagen and atelocollagen matrices were polymerized on rheometer plate at 4° C. for 5 minutes to get a baseline, and then the temperature was ramped up to 37° C. for polymerization. After 30 min of polymerization, the matrices formed were exposed to 5000 U/ml collagenase in an oscillatory shear-based, and strain-controlled time sweep experiment and tan of phase shift angle delta was tracked with respect to time as shown in FIG. 7. Absolute tan delta was plotted as a function of time and representative samples of each type of matrix are shown in this figure. Rise in tan delta value≥1 indicated phase change from solid to liquid, indicating complete proteolytic degradation of material. First derivative of tan delta was then plotted against time to get an inflection peak, which was used to calculate the total degradation time for matrices, after subtracting the first 30 minutes of polymerization time. Data analysis showed that degradation time required for matrices was significantly different for oligomer, telocollagen and atelocollagen matrices (p<0.05; N=3). The matrices degraded in the order of atelocollagen (138.0 min), followed by telocollagen (186.7 min), followed by oligomer (219.5 min) matrices, indicating that atelocollagen and oligomer matrices represented the extreme ends of the obtained proteolytic degradation spectrum. The results suggested that the use of atelocollagen, telocollagen, and oligomer as collagen building block can offer an opportunity to tune release kinetics of contained drug molecules owing to different proteolytic degradability and different fibril microstructure properties.

Based on the fibril microstructure and proteolytic degradation differences between various collagen building blocks, as reported previously, it was hypothesized that matrices formed from different collagen precursors will deliver molecules with different release kinetics. In order to test this hypothesis, 3 mg/ml polymerized matrices from oligomer, telocollagen and atelocollagen building blocks were formulated, containing 10 kDa and 2 MDa FITC-Dextran, at 0.25 mg/ml final concentration. The formulation was performed according to the procedure described above with respect to the formulation of collagen-fibril delivery devices (Example 1). Release kinetics from formulated delivery systems were then measured under two conditions: 1) in absence of collagenase, to investigate effect of microstructure on release kinetics (diffusion only); and 2) in presence of 125 U/ml collagenase, to investigate effect of both microstructure and proteolytic degradability on the release kinetics (diffusion+degradation).

Figure 8:
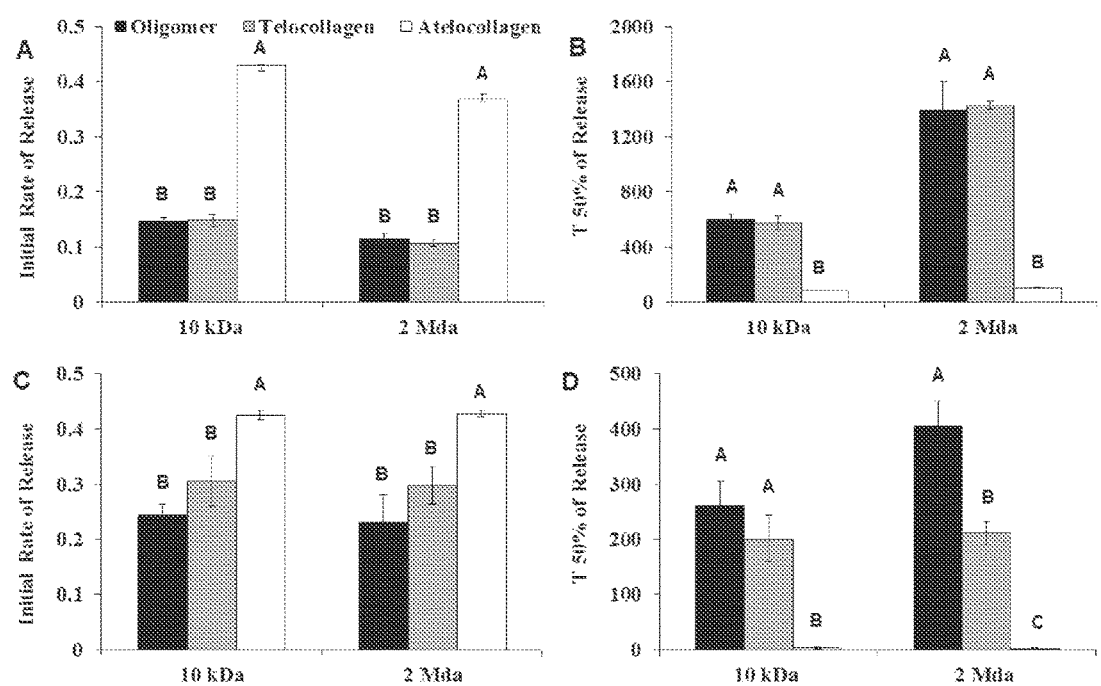
FIG. 8 represents data obtained from analyzing the molecular release of oligomer, telocollagen and atelocollagen matrices (3 mg/ml) polymerized with 10 kDa or 2 MDa FITC-dextran molecules as described in Example 4 of the present disclosure.

Referring now to FIG. 8, a graphical representation illustrating that the molecular release profiles are dependent upon the collagen polymer building blocks is shown. In particular, FITC-Dextrans with molecular sizes of 10 kDa and 2 MDa were polymerized within oligomer, telocollagen, and atelocollagen matrices (3 mg/ml). Time-dependent release profiles were monitored spectrofluorometrically in the absence (A,B) and presence (C,D) of collagenase (125 U/ml) and initial release rate (mean±SD; n=3; A,C) and T50% (mean±SD; n=3; B,D) quantified. For each panel, letters indicate statistically different experimental groups as determined by Tukey-Kramer range test. Results showed that in absence of collagenase, microstructure-based differences in the oligomer, telocollagen, and atelocollagen affected release kinetics parameters (FIGS. 8A and 8B). It was clear that the atelocollagen and oligomer were the building blocks that formed extreme ends of obtained release spectrum again.

In presence of collagenase, the rate of release was enhanced, due to proteolytic degradability in addition to collagen microstructure-based diffusion, both contributing to the molecular release. Interestingly, the proteolytic degradation as measured in the presence of collagenase emphasized differences in telocollagen and oligomer matrices in addition to those between oligomer and atelocollagen matrices. As seen in FIGS. 8C and 8D, a progressive increase in initial release rate and a progressive decrease in T50% values (p<0.05) was obtained for oligomer, telocollagen, and atelocollagen matrices in the presence of collagenase.

This experiment showed that collagen-fibril matrices composed of different building blocks demonstrated different molecular release profiles, due to the different fibril microstructure and different proteolytic degradation of matrices.

EXAMPLE 5

Deciphering Effect of Different Collagen Building Blocks on Release Mechanism of Molecules Using Weibull-function There are several empirical models available for simulating drug release from polymer matrices. Although the power law model has been extensively used, it is confined for the description of the first 60% of the release curve. The quality of the fit has been observed to be poor at longer time points where the cumulative release exceeds ~60%. Weibull function is another alternative that can be used for the description of release profiles based on the empirical use of the Weibull function described by the equation:

$$\frac{M_t}{M_\infty} = 1 - \exp(-\alpha t^b).$$

$M_t$ is the mass of drug released at time t, $M_\infty$ is the mass of drug released at infinite time (assumed equal to the amount of drug added), a denotes a scale parameter of time dependency, while b describes the shape of the dissolution curve progression. Papadopoulou et al. provided a powerful link between the shape parameter b and the diffusional mechanisms of the release, as shown in the Table 1 below (see, Papadopoulou V, Kosmidis K, Vlachou M, Macheras P: On the use of the Weibull function for the discernment of drug release mechanisms. *International journal of pharmaceutics* (2006) 309(1-2):44-50).

TABLE 1

Exponent b of Weibull function and mechanism of release

| b | Release mechanism-remarks |
|---|---|
| b < 0.35 | Not found in simulation and the experimental results. May occur in highly disordered spaces much different than the percolation cluster. |
| b ~0.35-0.39 | Diffusion in fractal substrate morphologically similar to the percolation cluster |
| 0.39 < b < 0.69 | Diffusion in fractal or disordered substrate different from the percolation cluster |
| b ~0.69-0.75 | Diffusion in normal Euclidian space |
| 0.75 < b < 1 | Diffusion in normal Euclidian substrate with contribution of another release mechanism |
| b = 1 | First order release obeying Fick's first law of diffusion; the rate constant a controls the release kinetics and the dimensionless solubility/dose ratio determines the final fraction of dose dissolved |
| b > 1 | Sigmoid curve indicative of complex release mechanism |

It was hypothesized that by fitting Weibull function to experimentally obtained release curves obtained with different soluble collagen-fibril building blocks, the underlying release mechanisms could be deciphered. Furthermore, by using Weibull function-based simulation of release kinetics in absence of collagenase condition, it should be validated how microstructure based differences alone caused by different interfibril branching capacity of collagen building blocks, affect their molecular release kinetics.

To this end, the Weibull function was incorporated into the experimental release kinetics obtained from commercial monomer collagen (BD rat tail), atelocollagen, telocollagen, and oligomer matrices admixed with various FITC-Dextran molecules. The Weibull function fit the experimental data well, and the parameter values a and b along with $R^2$ and confidence intervals determined for parameters a and b from the fits are given in Table 2 below.

Results show that commercial monomer (BD rat tail) matrices gave a diffusion based release mechanism, while oligomer and telocollagen collagen-fibril matrices showed a combined release mechanism (Fickian diffusion and Case II transport) associated with them. Atelocollagen showed completely different value of parameter b, perhaps indicating diffusional release mechanism as in highly disordered spaces. Thus, since Weibull function was fit to release kinetics in absence of collagenase alone, the results confirmed that collagen-fibril microstructure affects molecular release.

TABLE 2

Weibull function based parameters a and b for release kinetics from collagen matrices formulated from different building blocks (N = 3 for each matrix)

| BD Rat | a | b | R square | CI (a; b) |
|---|---|---|---|---|
| 2 MDa | 0.028348 | 0.533256 | 0.918419 | [0.0089, 0.4517; 0.04784, 0.6148] |
| 500 kDa | 0.021974 | 0.533584 | 0.932005 | [0.0107, 0.4728; 0.0332, 0.5943] |
| 40 kDa | 0.014174 | 0.608231 | 0.944953 | [0.0064, 0.5438; 0.0219, 0.6727] |
| 10 kDa | 0.017661 | 0.585925 | 0.951242 | [0.0089, 0.5279; 0.0263, 0.6439] |

Conclusion: Diffusion in normal Euclidian space for all molecular sizes

| Atelocollagen | A | b | R square | CI (a; b) |
|---|---|---|---|---|
| 2 MDa | 0.17026 | 0.328441 | 0.840058 | [0.0927, 0.2735; 0.2478, 0.3834] |
| 10 kDa | 0.281443 | 0.279144 | 0.808817 | [0.1668, 0.2296; 0.3961, 0.3287] |

Conclusion: May occur in highly disordered spaces much different than the percolation cluster

| Telomer | A | b | R square | CI (a; b) |
|---|---|---|---|---|
| 2 MDa | 0.001083 | 0.876103 | 0.954832 | [0.0002, 0.7883; 0.0019, 0.9639] |
| 500 kDa | 0.000405 | 0.984194 | 0.946009 | [2.1507e−05, 0.8744; 0.0008, 1.0939] |
| 40 kDa | 0.003291 | 0.778927 | 0.973534 | [0.0016, 0.7193; 0.0050, 0.8386] |
| 10 kDa | 0.008298 | 0.675238 | 0.973083 | [0.0047, 0.6244; 0.0118, 0.7260] |

Conclusion: Diffusion in normal Euclidian substrate with contribution of another release mechanism for all molecular sizes except 10 kDa, which shows diffusion in normal Euclidian space

| Oligomer | A | b | R square | CI (a; b) |
|---|---|---|---|---|
| 2 MDa | 0.001157 | 0.870807 | 0.942191 | [0.0002, 0.7715; 0.0021, 0.9701] |
| 500 kDa | 0.000473 | 0.96695 | 0.951171 | [5.3077e−05, 0.8640; 0.0009, 1.0699] |
| 40 kDa | 0.002865 | 0.795155 | 0.964108 | [0.0011, 0.7237; 0.0046, 0.8666] |
| 10 kDa | 0.006484 | 0.70258 | 0.963082 | [0.0030, 0.6401; 0.0099, 0.7650] |

Conclusion: Diffusion in normal Euclidian substrate with contribution of another release mechanism for all molecular sizes except 10 kDa, which shows diffusion in normal Euclidian space

EXAMPLE 6

Effect of Oligomer:Atelocollagen Ratio of Polymerization Kinetics

Figure 9:
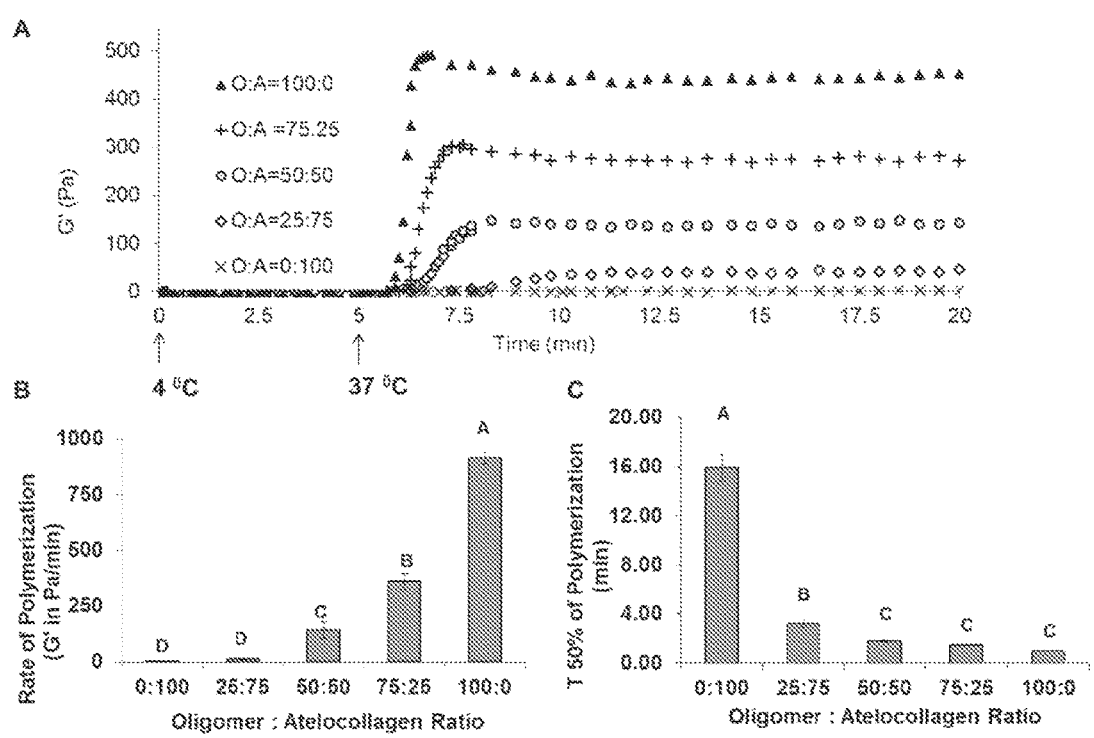
FIG. 9 depicts polymerization profile data obtained during the polymerization of collagen-fibril matrices as described in Example 6 of the present disclosure.

To determine if the oligomer:atelocollagen ratio had an effect on collagen-fibril matrix polymerization kinetics, the matrices were polymerized without FITC-Dextran on AR2000 Rheometer using the procedure described in Example 2. Five different matrix combinations were prepared by combining soluble oligomer and atelocollagen building block in the ratio of 0:100, 25:75, 50:50, 75:25, and 100:0 prior to polymerization. The resultant polymerization curves and calculated polymerization rates and T50% are shown in FIG. 9. In particular, time-dependent changes in shear-storage modulus were monitored as collagen formulations exhibited solution to matrix transition following an increase in temperature from 4° C. to 37° C. The polymerization profiles (A) were used to quantify initial rate of polymerization (mean±SD, B) and half-polymerization times (mean±SD, C) for N=3 of each matrix type.

It was observed from FIG. 9 that the different matrix combinations showed different polymerization profiles (p<0.05, N=3). Stiffness values of formed matrices increased as the percentage of oligomer increased (FIG. 9A). Rate of polymerization increased (FIG. 9B), and T50% decreased (FIG. 9C) with increasing oligomer content. Rapid polymerization times (T50%<5 minutes) were observed for all oligomer:atelocollagen ratios except 0:100.

Interestingly, all the matrix combinations displayed rapid polymerization (T50%<5 minutes), except the 0:100 oligomer:ateocollagen ratio (pure atelocollagen) matrix (FIG. 9C). Rapid collagen-fibril polymerization is an important design feature. In clinical applications, it is necessary that injected collagen solutions polymerize quickly to create a solid matrix that will allow for appropriate matrix placement and molecular delivery in situ, a feature, not exhibited by many conventional collagen formulations. These results indicated that with the use of different combinations of oligomer and atelocollagen building blocks, one can prepare matrices with different stiffness while retaining their potential to polymerize within 5 minutes (exception: 100% atelocollagen matrix).

EXAMPLE 7

Modulation of Matrix Release Kinetics by Varying the Compositional Ratio of Molecular Building Blocks Oligomer and Atelocollagen The different microstructures and proteolytic degradation obtained for matrices with different combinations of oligomer:atelocollagen ratios implied that the modulation in matrix composition would translate into its different agent release profiles. It was hypothesized that modulating the matrix composition using oligomer and atelocollagen building blocks could tune molecular release kinetics of low-fibril density matrices (3 mg/ml). In order to test this, collagen-fibril matrices were formulated with combinations of oligomer:atelocollagen in a ratio of 0:100, 5:95, 10:90, 15:85, 20:80, 25:75, 50:50, 75:25 and 100:0%. These matrices were admixed with 0.5 mg/ml of 1) 10 KDa FITC-Dextran molecules in one subset and 2) 2 MDa FITC-Dextran molecules in another subset, and their release was studied in absence or presence of 10 U/ml collagenase.

Figure 10:
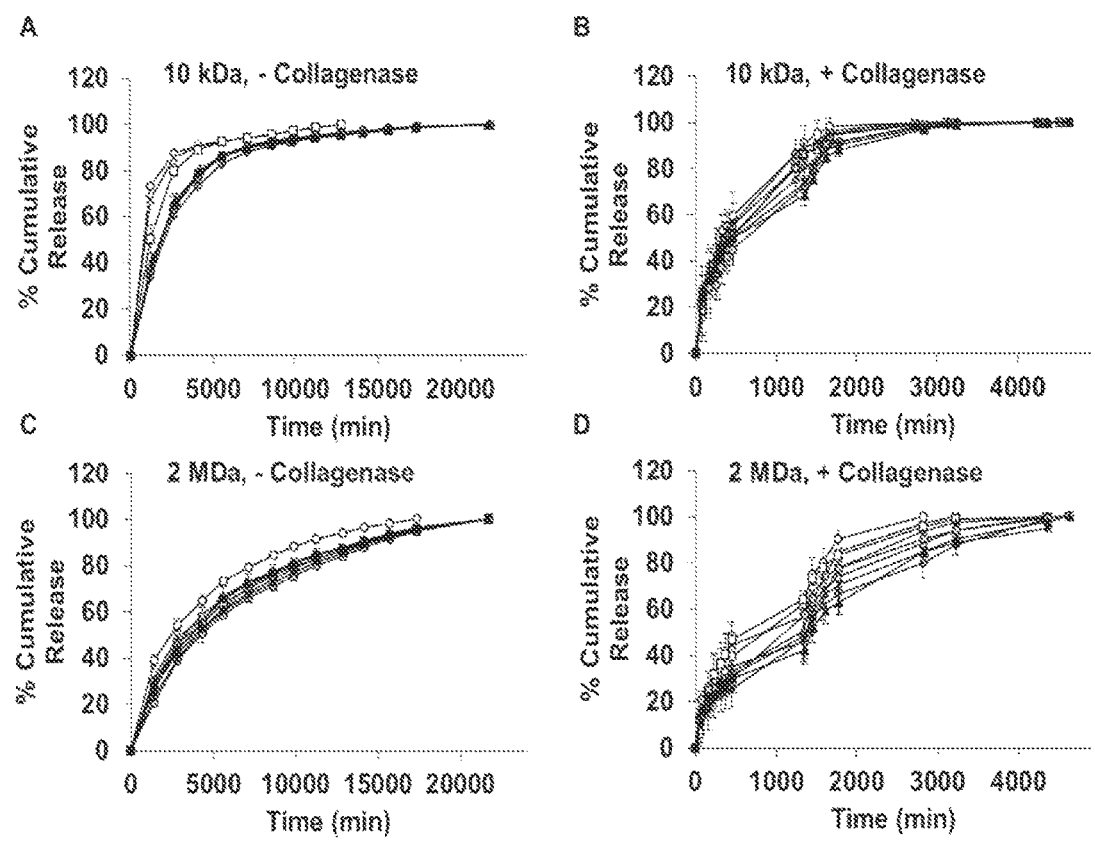
FIG. 10 represents time release profiles of small (10 kDa; panels A and B) and large (2 MDa; panels C and D) FITC-Dextran molecules polymerized within a variety of collagen-fibril matrices as described in Examples 7 and 10 of the present disclosure.

The results showed that low fibril-density (3 mg/ml) collagen matrices gave similar diffusional release profiles, (FIGS. 10A for 10 kDa, and 10C for 2 MDa) but different collagenase-dependent release profiles (FIGS. 10B for 10 kDa, and 10D for 2 MDa). The release profiles also showed enhanced time for complete release of 2 MDa FITC-Dextran compared to 10 KDa FITC-Dextran molecules (FIGS. 10C and D). This implied the tendency of matrices to retain larger sized molecules for longer time within them, than the smaller sized molecules.

EXAMPLE 8

Molecular Release from High-density Collagen-fibril Materials

It has been established previously that collagen-fibril density increases and pore size decreases with increasing soluble collagen building block concentration. It is also known that molecular diffusion and proteolytic degradation decrease with increase collagen-fibril density. As such, it was hypothesized that the release from the synthetic collagen-fibril matrices would be prolonged by increasing the concentration of pre-mixed soluble collagen building blocks. In order to test this, the oligomer collagen-fibril matrices were prepared at low (3 mg/ml) and high densities (15.6 mg/ml). Low-density matrices were prepared as described previously. High-density matrices were prepared by subjecting 3 mg/ml collagen-fibril matrices to confined compression to achieve 5.2× volume reduction. Cylinders of diameter 1.1 (thickness 2.6 mm) were prepared from each matrix type and release kinetics compared.

EXAMPLE 9

Creation of High-density Collagen-fibril Delivery Devices

Figure 14:
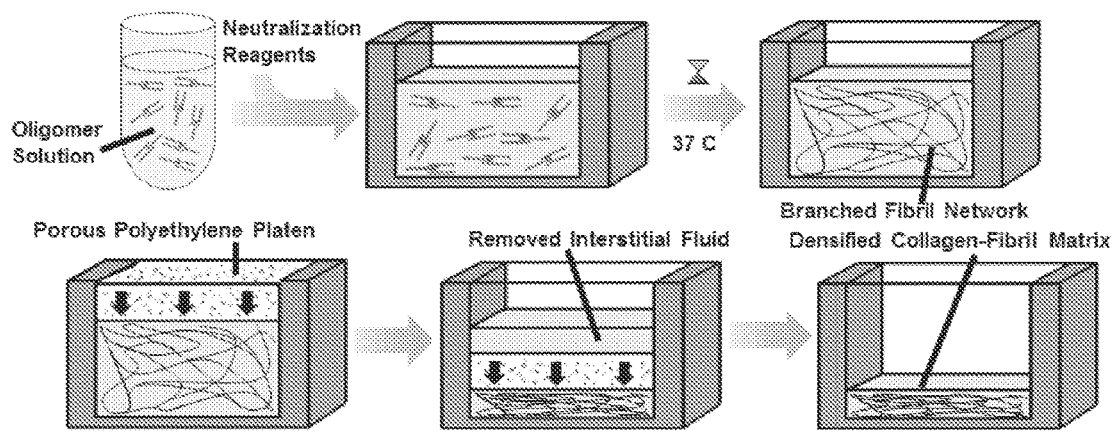
FIG. 14 depicts a schematic of a method of creating high density collagen-fibril matrices using confined compression as described in Example 9 of the present disclosure.

It was desired to create collagen matrices with increased fibril density without compromising their ability to support and induce cell infiltration and tissue regeneration. To this end, it has been shown that the oligomer matrices have an advantage in creating tissue-like materials without reducing porosity to an extent that cells cannot infiltrate it. Therefore, oligomer collagen matrices were densified as a proof-of-concept study. In particular, the effective oligomer concentration, which translates to fibril density, of the polymerized matrices was increased by the method of confined compression developed by Harbin laboratory. A schematic of the process for creating a high-fibril density matrix via confined compression in accordance with the teachings of the present invention is shown in FIG. 14. Briefly, 10.82 ml of soluble oligomer collagen (3 mg/ml) admixed with 2 MDa or 10 kDa FITC-Dextran was pipetted into compression molds (2 cm width by 4 cm length). The solutions were polymerized overnight at 37° C. to create collagen-fibril matrices with a thickness of 13.52 mm. The polymerized matrices with admixed FITC-Dextran were then subjected to confined compression using porous polyethylene platen (50 micron pore) at 6 mm/min to a final thickness 2.6 mm (2 cm width by 4 cm length). Final concentration of compressed collagen matrices was 15.6 mg/ml (5.2× compression). Cylinders of diameter 1.1 (thickness 2.6 mm) were prepared from low-density (3 mg/ml) and high-density (15.6 mg/ml) matrices. Molecular release profiles were measured in the presence of 50 U/ml collagenase for triplicate samples of each matrix formulation.

EXAMPLE 10

Figure 11:
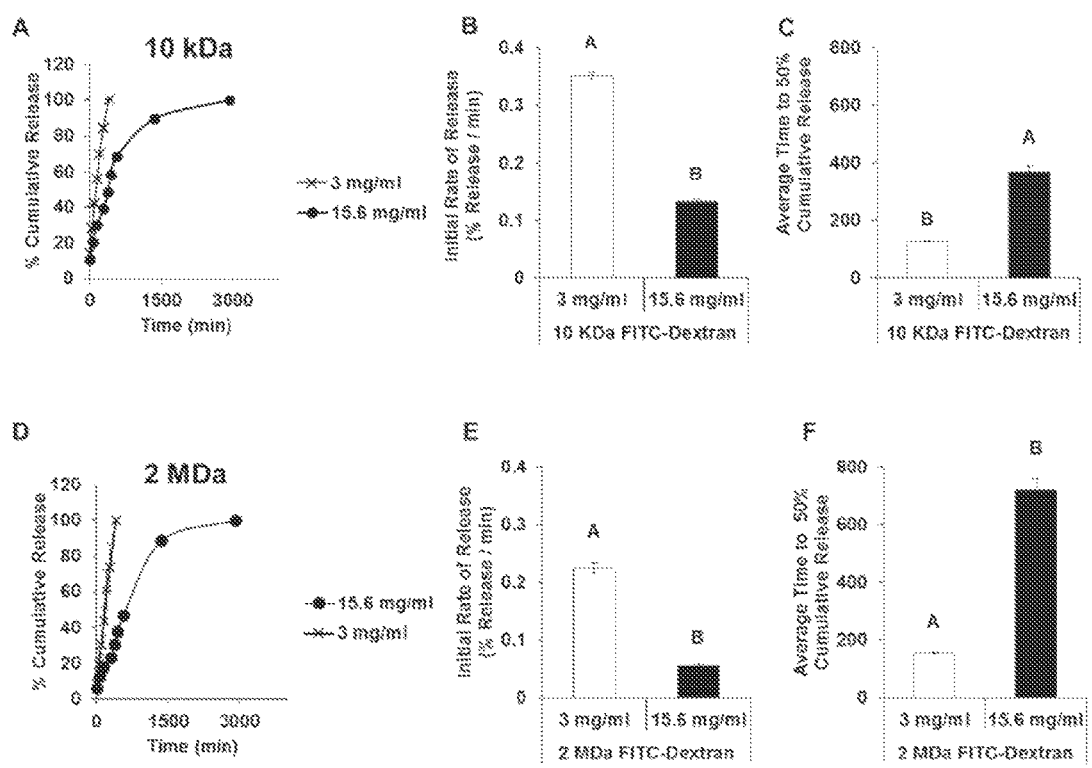
FIG. 11 depicts a summary of data obtained from FITC-dextran release from low-density (3 mg/ml) and high-density (15.6 mg/ml) collagen-fibril matrices in the presence of 50 U/ml collagenase as described in Example 10 of the present disclosure.
Figure 12:
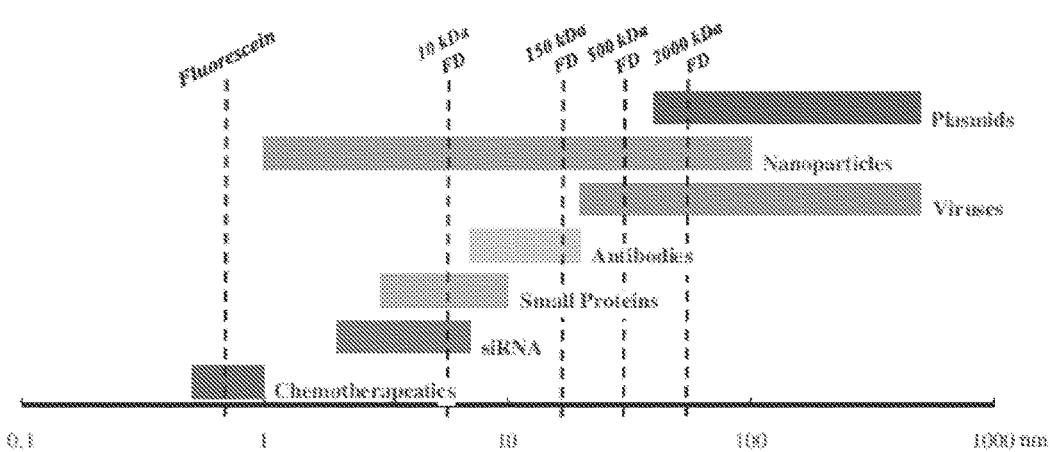
FIG. 12 depicts a schematic comparing the size of fluorescein and indicated FITC-dextran molecular weights relative to a variety of potential active agents in accordance with the teachings of present disclosure.
Figure 13:
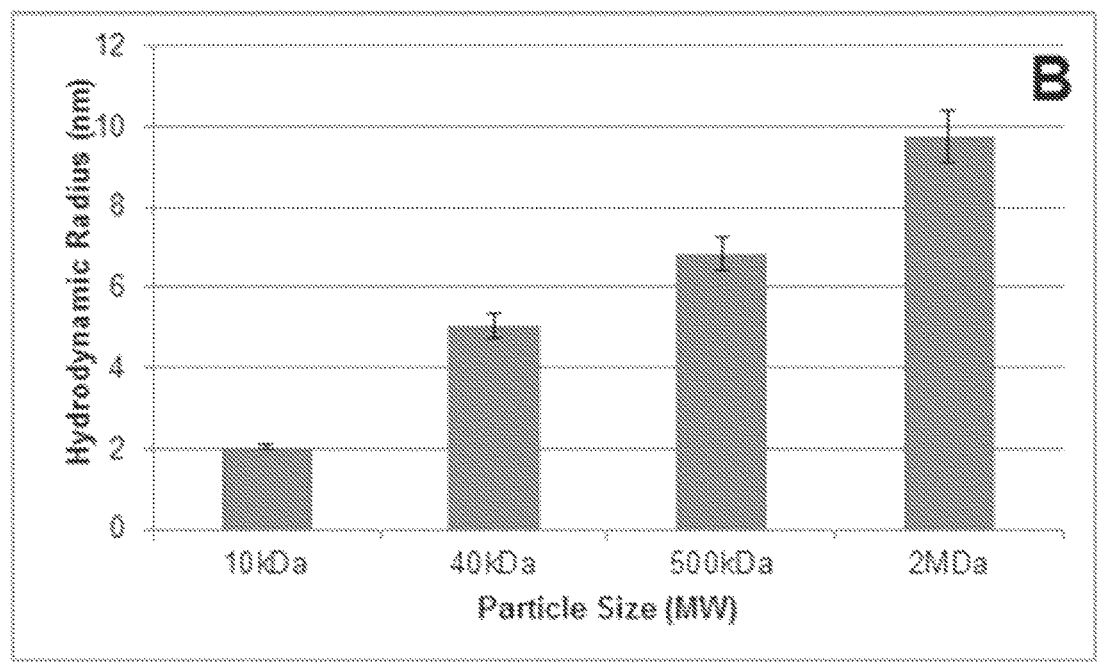
FIG. 13 depicts a previously published chart comparing FITC-Dextran particle size (MW) with hydrodynamic radius (nm)

Validating the Extension of Molecular Release from Densified Oligomeric Collagen The formulated collagen matrices of altered density (3 mg/ml=low; and 15.6 mg/ml=high) were compared for molecular release of 10 kDa and 2 MDa FITC-Dextran each, as shown in FIG. 11. In particular, 10 kDa and 2 MDa FITC-Dextran was admixed in 3 mg/ml and 15.6 mg/ml oligomer matrices. Release kinetics for both matrices were measured upon exposure to 50 U/ml collagenase. As expected, the difference between release profiles exhibited by low-density and high-density matrix formulation is enhanced for 2 MDa FITC-Dextran (D) as compared to 10 kDa FITC-Dextran (A). The initial rate of release is significantly lower in high density matrices compared to low density matrices for both 10 KDa (B) and 2 MDa (E) FITC-Dextrans. The T50% of release is significantly higher in high density matrices than in low density matrices for both smaller size FITC-Dextran (10 kDa) and larger size (2 MDa) as seen in FIGS. 10E and 10F. Results showed that FITC-Dextran release from compressed matrices was significantly more prolonged compared to non-compressed samples for both 10 KDa (FIG. 11A) and 2 MDa (FIG. 11D) FITC-Dextrans. A decrease in initial rate of release and an increase in T50% values, was also observed with higher collagen fibril density, for both 10 KDa (FIG. 11B, C) and 2 MDa (FIG. 11E, F) FITC-Dextrans. It was concluded from this experiment that densifying collagen matrices thus modulates molecular release from collagen-fibril matrices.

EXAMPLE 11

Effect of Density of Oligomer Collagen-fibril Matrices on Release of 10 kDa and 2 MDa FITC-dextran Release To further define the how the density of oligomer collagen-fibril matrices affects agent release, 10 kDa and 2 MDa FITC-dextrans were admixed at a concentration of 0.25 mg/ml within matrices prepared over the density range of 3 mg/ml to 40 mg/ml. Oligomer matrices prepared at 3 mg/ml were prepared as previously described in absence of confined compression, while 20 mg/ml and 40 mg/ml matrices were prepared by application of confined compression to 4.05 mg/ml matrices. Briefly, 10.39 ml and 20.78 ml of neutralized oligomer collagen (4.05 mg/ml) was admixed with 10 kDa or 2 MDa FITC-dextran (0.25 mg/ml) and pipetted into compression molds (2 cm width by 4 cm length). The solutions were polymerized overnight at 37° C. to form matrices of 1.3 cm and 2.6 cm thickness respectively. These matrices were then subjected to confined compression using a porous polyethylene platen to final thickness of 0.26 cm to achieve a 4.84× (20 mg/ml) and 9.88× (40 mg/ml) densification. Cylinders of diameter 1.1 (thickness 0.263 cm) were prepared from all matrices and used to measure release kinetics in the presence or absence of collagenase (10 U/ml). All measurements were made on triplicate samples. Release profiles were plotted and analyzed for time required for 50% cumulative release (T50%), which was calculated based on Weibull fit. The resultant Weibull parameters were used to define the release mechanism.

Figure 17:
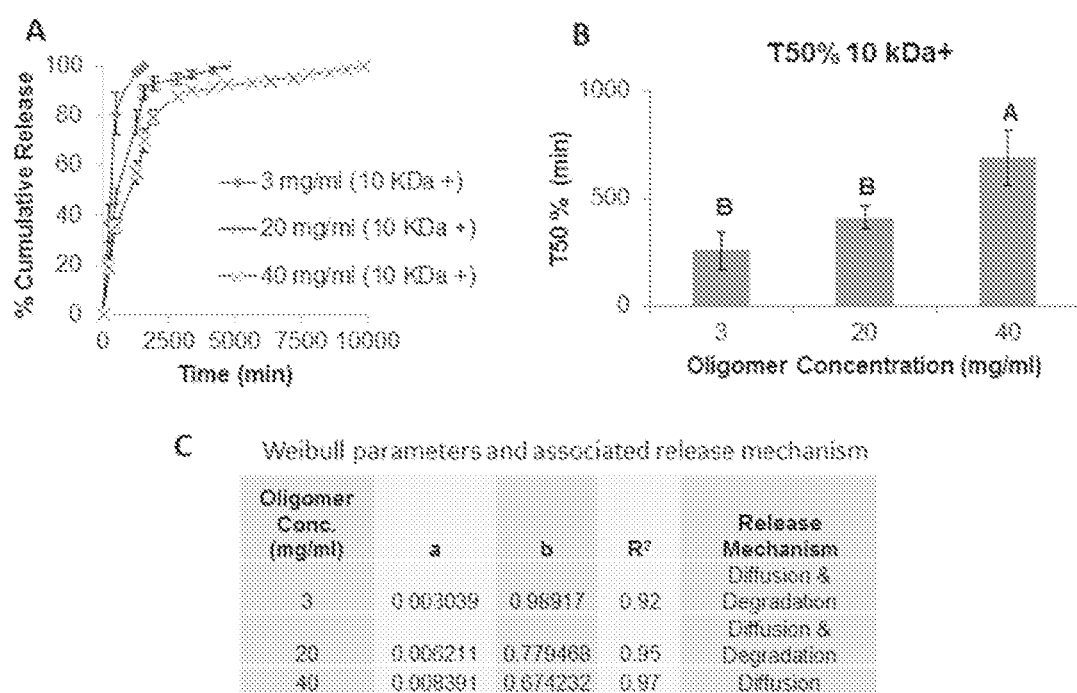
FIG. 17 depicts illustrative graphs showing a summary of data obtained for 10 kDa FITC-dextran release from oligomer collagen-fibril matrices prepared over a broad range of densities (3 to 40 mg/ml) in the absence of collagenase as described in Example 11 of the present disclosure.
Figure 19:
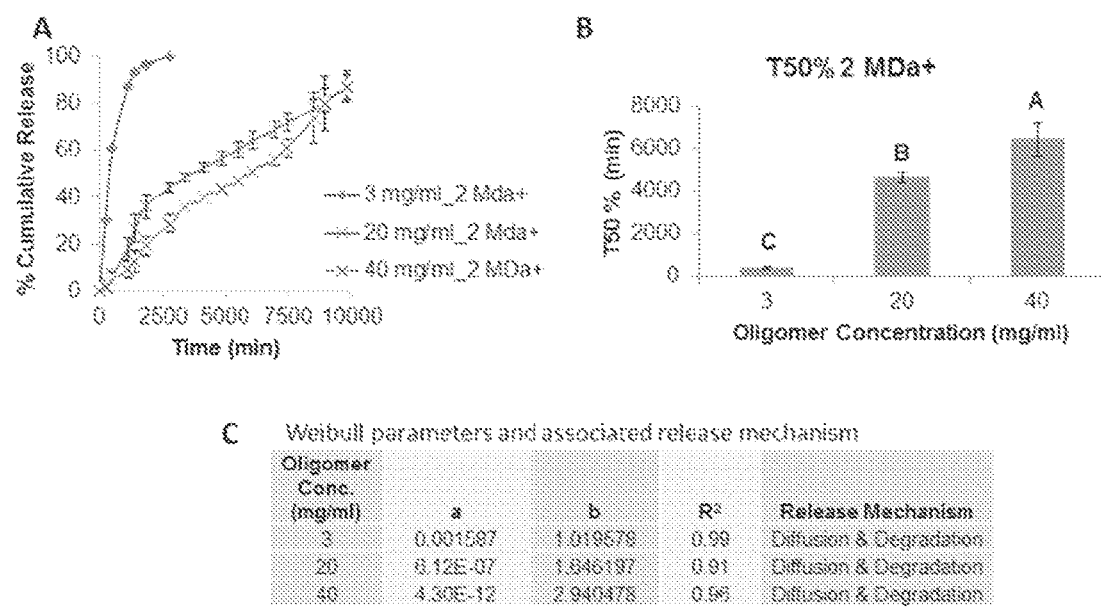
FIG. 19 depicts illustrative graphs showing a summary of data obtained for 2 MDa FITC-dextran release from oligomer collagen-fibril matrices prepared over a broad range of densities (3 to 40 mg/ml) in the presence of collagenase (10 U/ml) as described in Example 11 of the present disclosure.

The oligomer collagen-fibril matrices showed a density-dependent effect on molecular release of both 10 kDa and 2 MDa FITC-dextrans in the presence of 50 U/ml collagenase as shown in FIGS. 17 and 19. For both FITC-dextrans, an increase in T50% was observed with increased density. As expected, the dynamic range of density-dependent release was greatest for 2 MDa FITC-dextran. In addition, 10 kDa FITC-dextran showed decreased T50% values compared 2 MDa FITC-dextran for all matrices tested. Interestingly, Weibull analysis indicated that the 10 kDa release mechanisms for both 3 mg/ml and 20 mg/ml oligomer matrices involved both diffusion and degradation. On the other hand, the increased resistance to collagenase degradation demonstrated by 40 mg/ml oligomer matrices resulted in a diffusion only 10 kDa release mechanism. In contrast, all matrix formulations tested exhibited 2 MDa FITC-dextran release mechanisms governed by both diffusion and degradation.

Figure 18:
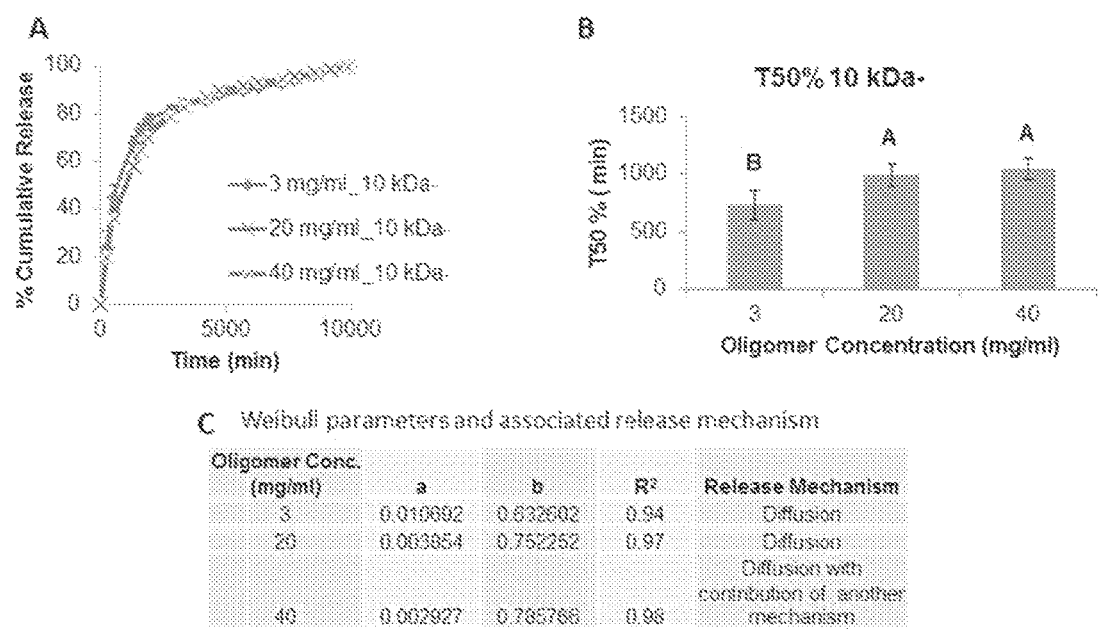
FIG. 18 depicts illustrative graphs showing a summary of data obtained for 10 kDa FITC-dextran release from oligomer collagen-fibril matrices prepared over a broad range of densities (3 to 40 mg/ml) in the presence of collagenase (10 U/ml) as described in Example 11 of the present disclosure.

Evaluation of density dependent release of 10 kDa FITC-dextran in absence of collagenase also showed a progressive increase in T50% values as a function with oligomer concentration or matrix density as shown in FIG. 18. As expected T50% values obtained in absence of collagenase were less than those measured in the presence of collagenase (FIG. 17). Weibull parameters indicated that 10 kDa FITC-dextran release involved primarily diffusion for 3 mg/ml and 20 mg/ml, while release from 40 mg/ml matrices involved diffusion and some other mechanism. This experiment further validated and defined how densifying collagen matrices modulate molecular release from collagen-fibril matrices.

EXAMPLE 12

Preparation and Characterization of Collagen Polymers

Market weight porcine hides were obtained from commercial meat-processing sources according to Purdue University Animal Care and Use Committee (PACUC) guidelines. Oligomeric collagen was extracted from the dermis as described previously (Kreger et al, (2010) *Biopolymers* 93:690-707, herein incorporated by reference). Monomer-rich (telocollagen) collagen was prepared by extracting pig skin with 0.5 M acetic acid followed by salt precipitation. Telopeptide regions within the collagen molecule, which contain intermolecular cross-linking sites, were enzymatically removed by complete pepsin digestion. All collagens were dialyzed exhaustively against 0.1 M acetic acid and then lyophilized. Prior to use, lyophilized collagens were dissolved in 0.01 N HCl. All collagens were rendered aseptic by exposure to chloroform overnight at 4° C. Collagen concentration was determined using a Sirius Red (Direct Red 80) assay. The collagen formulations were standardized based upon purity as well as polymerization capacity. Here, polymerization capacity is defined as the relationship between the shear storage modulus (G') of the polymerized matrices and the collagen content of the polymerization reaction. Commercial monomer collagen, acid solubilized type I collagen harvested from rat tails was purchased from BD Biosciences (Bedford, Mass., referenced as BD-rat tail collagen, BD-RTC).

EXAMPLE 13

Preparation of Collagen-Fibril Matrices

For preparation of 3D collagen fibrillar matrices, collagens were diluted in 0.01N HCl and further neutralized with phosphate buffered saline (PBS, 10×, pH 7.4) and 0.1N sodium hydroxide (NaOH) to achieve neutral pH (7.4) and a final collagen concentration of 3 mg/ml. For formulating matrices with FITC-Dextran, a similar polymerization process was applied and FITC-Dextran (10 kDa, 40 kDa, 500 kDa, or 2 MDa Invitrogen, Eugene, Oreg.) was predissolved in 10×PBS to yield a final concentration of 0.5 mg/ml within the polymerized matrix. Preparation of matrices with varied oligomer:monomer ratios involved neutralization of each component at 3 mg/ml with 0.5 mg/ml FITC-Dextran and then varying the volume ratio to achieve 0:100, 25:75, 50:50, 75:25, and 100:0 prior to polymerization.

The neutralized collagen solutions were kept on ice prior to the induction of polymerization by warming to 37° C. In other experiments the temperature of the rheometer plate was maintained below 10° C. for a period of 5 minutes to get the baseline storage modulus of non-polymerized matrices and then increased to 37° C. Due to the increased viscosity of the collagen solutions, positive displacement pipettes (Microman, Gilson, Middleton, Wis.) were used to accurately pipet all collagen solutions. To confirm that the addition of FITC-Dextran had no effect on collagen polymerization kinetics and matrix physical properties, matrices were prepared in the absence and presence of FITC-Dextrans (10 KDa and 2 MDa, 0.5 mg/ml). Time-dependent changes in viscoelastic properties (shear storage modulus (G'), shear loss modulus (G"), and phase shift delta (/5) during polymerization were measured in oscillatory shear using an AR2000 rheometer (TA Instruments, New Castle, Del.) adapted with a stainless steel 40 mm diameter parallel plate geometry). Polymerization kinetics and viscoelastic properties for matrices prepared in the presence and absence of FITC-dextran then were compared.

EXAMPLE 14

Measurement of Release Kinetics

Collagen matrices (3 mg/ml) containing various sized FITC-Dextran at a concentration of 0.5 mg/ml were polymerized in 48-well plates (250 J.lllwell). Samples then were overlaid with 750 µl PBS, pH 7.4 containing no collagenase or 125 U/ml bacteria *Clostridium histolyticum* collagenase (CLS4, Worthington Biomchemical Corporation, Lakewood, N.J.). Plates were subjected to gradual rotation at 60 rpm on a Fisher Scientific Clinical Rotator. The supernatant from each sample was collected at specific time intervals and replaced with fresh solutions. Sampling intervals were predicted based on simulated release curves for each molecule size, modeled using diffusion equation given by Siepmann et al. A spectrofluorometer (Molecular Devices Spectramax M5) was used to measure fluorescence at an excitation and emission wavelength of 493 and 530 nm respectively. This process was repeated until Relative Fluorescence Units from supernatant of wells matched baseline fluorescence (PBS plus/minus collagenase containing no FITC-Dextran), indicating completion of the FITC-Dextran release.

The data collected were used to plot % Cumulative release vs time in minutes. Two parameters were used to define release curves—rate of release and T50% of Release. Initial rate of release was defined as the slope of the release curve analyzed over time required for reaching 25% of cumulative release, obtained using linear trendline fit in Microsoft Excel. T50% of Release, defined as time required to obtain 50% of Cumulative Release, was obtained from power best fits of release curves in Matlab (Mathworks).

All statistical analyses were performed in MiniTab. The comparison between collagenase and PBS was performed with a 2-sample Student's T-Test with a confidence interval of 95%. The comparisons between drug size and matrix composition were performed with ANOVA and post-hoc Tukey test with a 95% confidence interval.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A collagen-based therapeutic delivery device, comprising:
   a controlled release collagen-based therapeutic delivery device, the device including:
   an insoluble synthetic collagen-fibril matrix comprising a polymerization product of soluble oligomeric collagen or a polymerization product of a mixture of soluble oligomeric collagen with one or more types of non-oligomeric soluble collagen molecules; and
   a first active agent dispersed throughout the collagen-fibril matrix or within a portion of the collagen-fibril matrix; wherein the first active agent is present in a biologically active amount;
   wherein the collagen-fibril matrix exhibits a stiffness of at least 5 Pa; and
   wherein the microstructure of the collagen-fibril matrix controls the release kinetics of the first active agent in the collagen-based therapeutic delivery device, and wherein the device does not include cells.

2. The therapeutic delivery device of claim 1, wherein the collagen-fibril matrix comprises type I collagen.

3. The therapeutic delivery device of claim 1, wherein the collagen-based therapeutic delivery device is a tissue graft.

4. The therapeutic delivery device of claim 1, wherein the collagen-based therapeutic delivery device is lyophilized.

5. The therapeutic delivery device of claim 1, wherein the collagen-fibril matrix comprises a polymerization product of a mixture of more than 0 but less than 100 percent soluble oligomeric collagen with more than 0 but less than 100 percent of one or more types of non-oligomeric soluble collagen molecules.

6. The therapeutic delivery device of claim 5, wherein the collagen-fibril matrix comprises a polymerization product of a mixture of soluble oligomeric collagen with one or more types of non-oligomeric soluble collagen molecules and wherein the oligomeric collagen and non-oligomeric soluble collagen molecules are in a ratio within a range selected from the group consisting of 5:95 to 10:90, 10:90 to 15:85, 15:85 to 20:80, 20:80 to 25:75, 25:75 to 50:50, and 50:50 to 75:25.

7. The therapeutic delivery device of claim 1, further comprising a second active agent dispersed throughout the collagen-fibril matrix or within a portion of the collagen-fibril matrix.

8. The therapeutic delivery device of claim 7, wherein each of the first and second active agents is a growth factor or a drug.

9. The therapeutic delivery device of claim 1, wherein the collagen-fibril matrix includes a first portion having a first fibril density and a second portion having a second fibril density; wherein the first fibril density is different than the second fibril density.

10. The therapeutic delivery device of claim 1, wherein the collagen-fibril matrix includes a first portion having dispersed therein the first active agent and a second portion having dispersed therein a second active agent, wherein the therapeutic delivery device exhibits a first release profile for the first active agent and a second release profile for the second active agent, and wherein the first release profile is different than the second release profile.

11. The therapeutic delivery device of claim 1, wherein the first active is present in in a biologically active amount sufficient to act as a chemotherapeutic agent, an oncostate, a hemapoietic modulator, an immune modulator, or an osteoinductant.

12. The therapeutic delivery device of claim 1, wherein the collagen-fibril matrix includes a first portion having a first fibril microstructure and a second portion having a second fibril microstructure.

13. The therapeutic delivery device of claim 1, wherein the polymerization product includes at least one of telocollagen and atelocollagen.

* * * * *

UNITED STATES PATENT AND TRADEMARK OFFICE
CERTIFICATE OF CORRECTION

PATENT NO. : 10,314,940 B2
APPLICATION NO. : 15/505046
DATED : June 11, 2019
INVENTOR(S) : Sherry Voytik-Harbin and Rucha Joshi It is certified that error appears in the above-identified patent and that said Letters Patent is hereby corrected as shown below:

On the Title Page

Item [12], should read Voytik-Harbin et al.

Item [72], insert --Rucha Joshi, Davis, California (US)--

Signed and Sealed this
Ninth Day of August, 2022

Katherine Kelly Vidal
*Director of the United States Patent and Trademark Office*